(12) United States Patent
McCormick et al.

(10) Patent No.: US 7,939,318 B2
(45) Date of Patent: May 10, 2011

(54) FLEXIBLE VACCINE ASSEMBLY AND VACCINE DELIVERY PLATFORM

(75) Inventors: Alison A. McCormick, Vacaville, CA (US); Mark L. Smith, Davis, CA (US); Kenneth E. Palmer, Vacaville, CA (US); John A. Lindbo, Vacaville, CA (US); Long V. Nguyen, Vacaville, CA (US); Gregory P. Pogue, Vacaville, CA (US)

(73) Assignee: Kentucky Bioprocessing, LLC, Owensboro, KY (US)

( * ) Notice: Subject to any disclaimer, the term of this patent is extended or adjusted under 35 U.S.C. 154(b) by 763 days.

(21) Appl. No.: 11/410,572

(22) Filed: Apr. 24, 2006

(65) Prior Publication Data
US 2006/0188991 A1 Aug. 24, 2006

Related U.S. Application Data

(63) Continuation of application No. 10/457,082, filed on Jun. 6, 2003, now abandoned.

(60) Provisional application No. 60/386,921, filed on Jun. 7, 2002.

(51) Int. Cl.
*C12N 15/63* (2006.01)
*A61K 35/00* (2006.01)

(52) U.S. Cl. .................................. 435/320.1; 424/93.1

(58) Field of Classification Search ........................ None
See application file for complete search history.

(56) References Cited

U.S. PATENT DOCUMENTS

| | | | |
|---|---|---|---|
| 5,443,969 A * | 8/1995 | Wilson et al. ............... | 435/91.32 |
| 5,667,782 A | 9/1997 | Roy ........................... | 424/192.1 |
| 5,795,754 A | 8/1998 | Ludmerer et al. ......... | 435/172.3 |
| 5,877,159 A | 3/1999 | Powell et al. | |
| 5,977,438 A | 11/1999 | Turpen et al. ............. | 800/288 |
| 6,033,895 A | 3/2000 | Garger et al. | |
| 6,037,456 A | 3/2000 | Garger et al. | |
| 6,228,423 B1 | 5/2001 | Sokoll et al. | |
| 6,232,099 B1 | 5/2001 | Chapman et al. | |
| 6,261,765 B1 | 7/2001 | McCarthy et al. ......... | 435/5 |
| 6,303,779 B1 | 10/2001 | Garger et al. | |
| 6,328,972 B1 | 12/2001 | Rock | |
| 6,420,160 B1 | 7/2002 | Bloch .......................... | 435/239 |
| 6,503,732 B1 | 1/2003 | Fitchen et al. .............. | 435/69.1 |
| 6,589,529 B1 | 7/2003 | Choi et al. .................. | 424/186.1 |
| 6,703,306 B2 | 3/2004 | Lee ............................. | 438/649 |
| 7,033,749 B2 * | 4/2006 | Pasloske et al. ............ | 435/5 |
| 7,351,533 B2 * | 4/2008 | McCarthy et al. .......... | 435/6 |
| 2002/0081295 A1 | 6/2002 | Schiller et al. ............. | 424/143.1 |
| 2003/0054010 A1 | 3/2003 | Sebbel et al. ............... | 424/185.1 |
| 2003/0072753 A1 | 4/2003 | Schiller et al. ............. | 424/140.1 |
| 2003/0099668 A1 | 5/2003 | Bachmann et al. ........ | 424/204.1 |
| 2006/0286099 A1* | 12/2006 | Swain et al. ............... | 424/133.1 |

FOREIGN PATENT DOCUMENTS

| | | |
|---|---|---|
| WO | WO 92/18618 | 10/1992 |
| WO | WO 95/21248 | 8/1995 |
| WO | WO9724447 A1 | 7/1997 |
| WO | WO 97/46693 | 12/1997 |
| WO | WO0023955 | 4/2000 |
| WO | WO 00/32227 | 6/2000 |
| WO | WO0131046 A1 | 5/2001 |
| WO | WO0166778 A2 | 9/2001 |
| WO | WO0185208 A2 | 11/2001 |
| WO | WO0200250 A2 | 1/2002 |

OTHER PUBLICATIONS

Buonaguro et al. High efficient production of Pr55(gag) virus-like particles expressing multiple HIV-1 epitopes, including a gp120 protein derived from an Ugandan HIV-1 isolate of subtype A. Antiviral Res. Jan. 2001;49(1):35-47.*
Gallie, D.R., et al; In Vivo Uncoating and Efficient Expression of Foreign mRNAs Packaged in TMV-Like Particles; Science; May 29, 1987; pp. 1122-1124; US, vol. 236.
Koo, Moses, et al; Protective Immunity Against Murine Hepatitis Virus (MHV) Induced by Intranasal or Subcutaneous Administration of Hybrids of Tobacco Mosaic Virus That Carries an MHV Epitope; Proceedings of the National Academy of Sciences of the United States of America; Jul. 6, 1999; pp. 7774-7779 vol. 96.
Brennan, Frank R., et al; Cowpea Mosaic Virus as a Vaccine Carrier of Heterologous Antigens; Molecular Biotechnology; 2001; pp. 15-26; vol. 17.
Nemchinov, L.G., et al; Development of a Plant-Derived Subunit Vaccine Candidate Against Hepatitis C Virus; Archives of Virology; 2000; pp. 2557-2573; vol. 145.
Adams, S.E., et al; The expression of hybrid HIV:Ty Virus-like Particles in Yeast; Nature; Sep. 3, 1987; pp. 68-70; vol. 329. Martin F.
Bachmann, et al., *The Influence of Antigen Organization on B Cell Responsiveness*, Science (Nov. 1993) 262:1448-1451, American Association for Advancement of Science, USA.
Thomas Fehr et al., *T Cell-independent Type I Antibody Response Against B cell Epitopes Expressed Repetitively on Recombinant Virus Particles*, Proc. Natl. Sci. USA (Aug. 1998) 95:9477-9481, The National Academy of Sciences.
Martin Bachmann, et al., *Cutting Edge Commentary: Immune Responses in the Absence of Costimulation: Viruses Know the Trick*, The Journal of Immunology, (1998) 161:5791-5794, American Association of Immunologists. (The year of publication is sufficiently earlier than the effective U.S. filing date and any foreign priority date so that the particular month of publication is not in issue.).
Tazio Storni, et al., *Critical Role for Activation of Antigen-Presenting Cells in Priming of Cytotoxic T Cell Responses After Vaccination with Virus-Like Particles*, The Journal of Immunology (Mar. 2002) 168:2880-2886, American Association of Immunologists.

(Continued)

Primary Examiner — Michele K Joike
(74) Attorney, Agent, or Firm — Wyatt, Tarrant & Combs, LLP

(57) ABSTRACT

Herein-described are various methods for making a vaccine that are made of re-assembled virus like particles (VLP). First, the VLPs are disassembled into encapsidation intermediate populations. Each encapsidation intermediate population undergoes, for instance, chemical conjugation of unique peptide or nucleic moieties to form separate populations. Thereafter, a predetermined amount of each of the several (one or more) different encapsidation intermediates from the different populations is mixed and joined, forming intact VLPs, surrounding a nucleic acid core, that are composed of different encapsidation intermediate such that the reassembled VLP displays more than one peptide or nucleic acid. The nucleic acid can function either as a scaffold alone or can be engineered for the expression of an immunomodulatory protein in a eukaryotic cell.

3 Claims, 25 Drawing Sheets

OTHER PUBLICATIONS

Andrea Jegerlehner, et al., *A Molecular Assembly System that Renders Antigens of Choice Highly Repetitive for Induction of Protective B Cell Responses*, Vaccine (Aug. 2002) 20:3104-3112, Elsevier Science Ltd.

Koo et al. Protective immunity against murine hepatitis virus (MHV) induced by intranasal or subcutaneous administration of hybrids of tobacco mosaic virus that caries an MHV epitope. PNAS (1999), vol. 96, pp. 7774-7779.

Fitchen et al. Plant virus expressing hybrid coat protein with added murine epitope elicits autoantibody response. Vaccine (1995), vol. 13, No. 12, pp. 1051-1057.

Fitchen, John, et al; Plant Virus Expressing Hybrid Coat Protein with Added Murine Epitope Elicits Autoantibody Response;Vaccine, vol. 13, No. 12, pp. 1051-1057; 1995; Elsevier Science Ltd.

* cited by examiner

FIG 2

```
┌─────────────────────────────────┐
│ S5: TMV virus                   │
│ with activated conjugation site │
└─────────────────────────────────┘
                │
                ▼
┌─────────────────────────────────┐
│ S6: TMV virus isolations        │
└─────────────────────────────────┘
                │
                ▼
┌─────────────────────────────────┐
│ S7: Dissociation of TMV virus   │
└─────────────────────────────────┘
                │
                ▼
┌─────────────────────────────────┐
│ S8: Formation of TMV 20S disks  │
└─────────────────────────────────┘
                │
                ▼
┌──────────────────────────────────────┐
│ S9: Conjugation of immune or functional │
│ peptides or nucleic acids to separate │
│ 20S disk populations:                │
└──────────────────────────────────────┘
        ↙           ↓           ↘
┌──────────────┐ ┌──────────────┐ ┌──────────────┐
│ 20S displaying│ │ 20S displaying│ │ 20S displaying│
│ peptide 1    │ │ peptide 2    │ │ peptide 3    │
└──────────────┘ └──────────────┘ └──────────────┘
        ↘           ↓           ↙
┌──────────────────────────────────────┐
│ S10: In vitro reassembly of TMV VLP  │
│ Using 20S disk populations and       │
│ RNA molecule containing TMV ori      │
└──────────────────────────────────────┘
                │
                ▼
┌──────────────────────────────────────┐
│ P2: Multivalent VLP Vaccine Immunogen│
│ Composed of TMV VLPs, each displaying│
│ Peptides 1, 2 and 3 and containing RNA│
│ for bifunctional vaccine             │
└──────────────────────────────────────┘
```

FIG 4

S15: Individual TMV viruses with single genetic peptide fusion
Peptide 1
Peptide 2
Peptide 3
Separately isolated and prepared

↓

TMV virus-1 | TMV virus-2 | TMV virus-3

↓

S16: Separate dissociation of TMV virus 1,2,3

↓

S17: Formation of TMV 20S disks for fusion 1,2,3

↓

S18: In vitro reassembly of TMV VLP Using 20S disk populations and RNA molecule containing TMV ori

↓

P4: Multivalent VLP Vaccine Immunogen Composed of TMV VLPs, each displaying Peptides 1, 2 and 3 and containing RNA for bifunctional vaccine

DNA sequence (Seq ID No: 19)
ATG*GGATGTGGA*TCTTACAGTATCACTACTCCATCTCAGTTCGTGTTCTTGTCATCAGC
GTGGGCCGACCCAATAGAGTTAATTAATTTATGTACTAATGCCTTAGGAAATCAGTT
TCAAACACAACAAGCTCGAACTGTCGTTCAAAGACAATTCAGTGAGGTGTGGAAACC
TTCACCACAAGTAACTGTTAGGTTCCCTGACAGTGACTTTAAGGTGTACAGGTACAA
TGCGGTATTAGACCCGCTAGTCACAGCACTGTTAGGTGCATTCGACACTAGAAATAG
AATAATAGAAGTTGAAAATCAGGCGAACCCCACGACTGCCGAAACGTTAGATGCTA
CTCGTAGAGTAGACGACGCAACGGTGGCCATAAGGAGCGCGATAAATAATTTAATA
GTAGAATTGATCAGAGGAACCGGATCTTATAATCGGAGCTCTTTCGAGAGCTCTTCT
GGTTTGGTTTGGACCTCTGGTCCTGCAACTTGA Amino acid translation
MG*CG*SYSITTPSQFVFLSSAWADPIELINLCTNALGNQFQTQQARTVVQRQFSEVWKPSP
QVTVRFPDSDFKVYRYNAVLDPLVTALLGAFDTRNRIIEVENQANPTTAETLDATRRVD
DATVAIRSAINNLIVELIRGTGSYNRSSFESSSGLVWTSGPAT (2)

DNA sequence (Seq ID No: 20)
ATG*GGAAAAGGA*TCTTACAGTATCACTACTCCATCTCAGTTCGTGTTCTTGTCATCAGC
GTGGGCCGACCCAATAGAGTTAATTAATTTATGTACTAATGCCTTAGGAAATCAGTT
TCAAACACAACAAGCTCGAACTGTCGTTCAAAGACAATTCAGTGAGGTGTGGAAACC
TTCACCACAAGTAACTGTTAGGTTCCCTGACAGTGACTTTAAGGTGTACAGGTACAA
TGCGGTATTAGACCCGCTAGTCACAGCACTGTTAGGTGCATTCGACACTAGAAATAG
AATAATAGAAGTTGAAAATCAGGCGAACCCCACGACTGCCGAAACGTTAGATGCTA
CTCGTAGAGTAGACGACGCAACGGTGGCCATAAGGAGCGCGATAAATAATTTAATA
GTAGAATTGATCAGAGGAACCGGATCTTATAATCGGAGCTCTTTCGAGAGCTCTTCT
GGTTTGGTTTGGACCTCTGGTCCTGCAACTTGA Amino acid translation
MG*KG*SYSITTPSQFVFLSSAWADPIELINLCTNALGNQFQTQQARTVVQRQFSEVWKPSP
QVTVRFPDSDFKVYRYNAVLDPLVTALLGAFDTRNRIIEVENQANPTTAETLDATRRVD
DATVAIRSAINNLIVELIRGTGSYNRSSFESSSGLVWTSGPAT

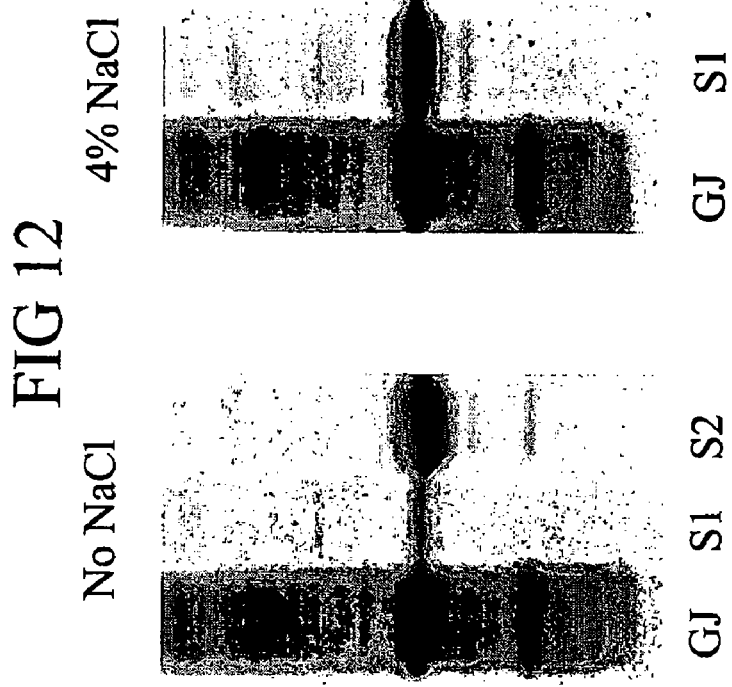

FIG 15
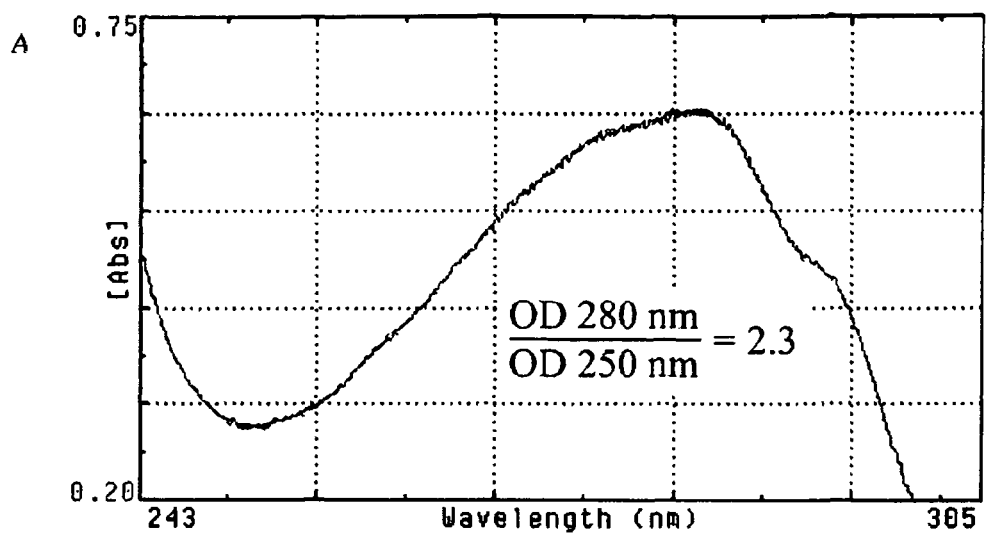
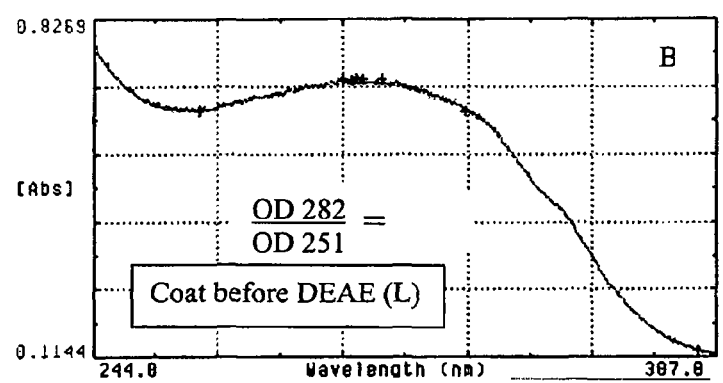
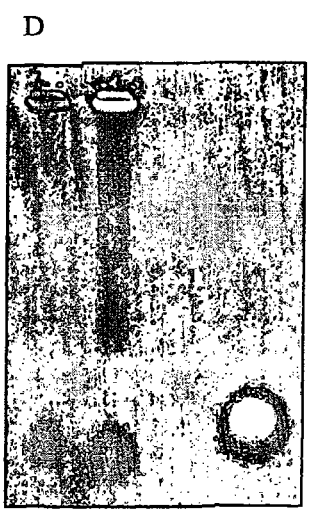
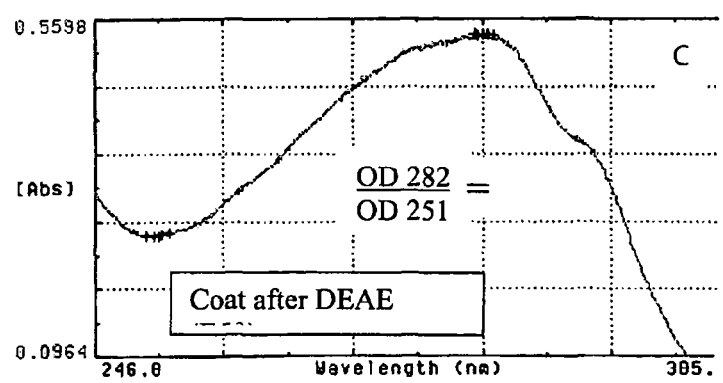
L   FT   E50

FIG 17
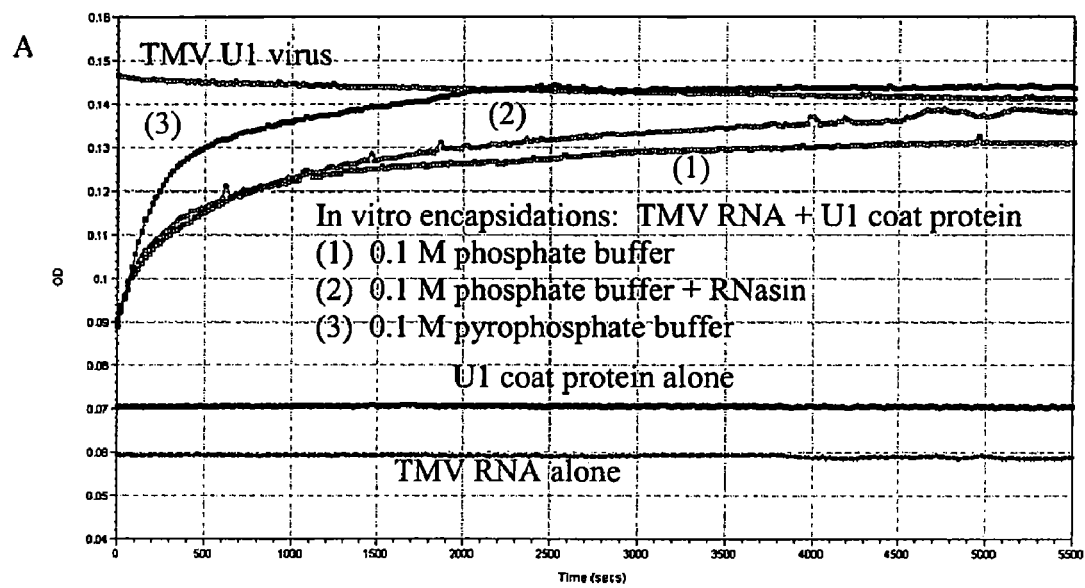
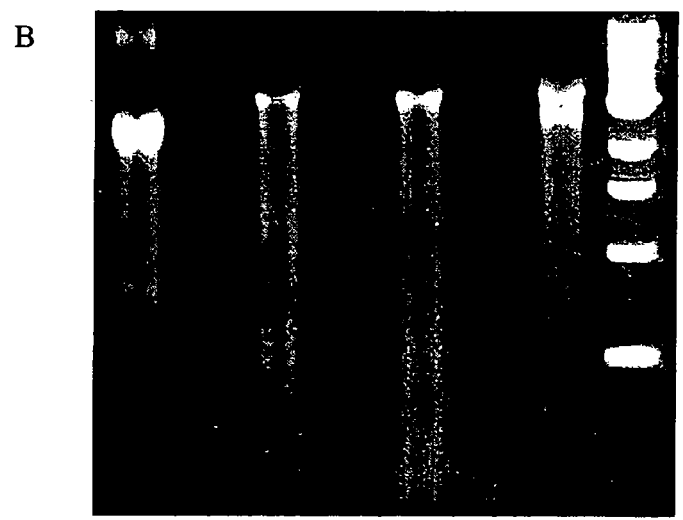

FIG 18

FIG 19
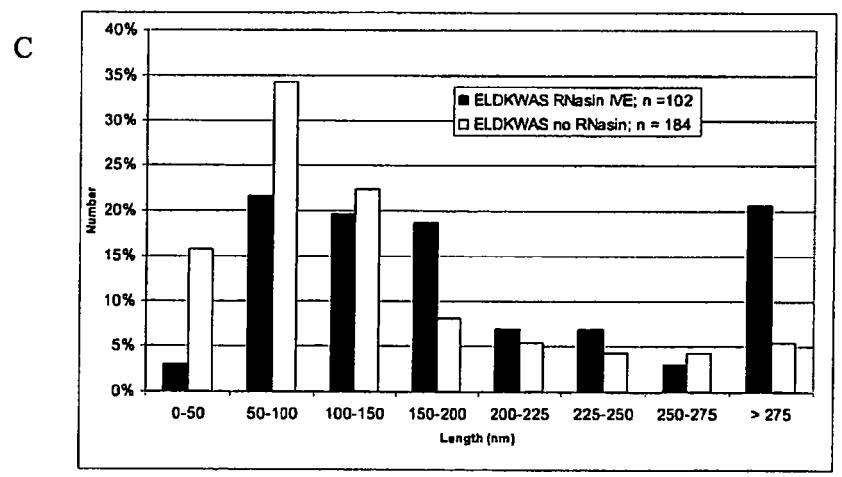

FIG 21
A  Lot ID- CRPV 2.1 LSBC030326-UT
Sequence weight= 19320 (Met cleaved, ave mass)
MALDI-TOF MS MW= 19320 (ave mass)
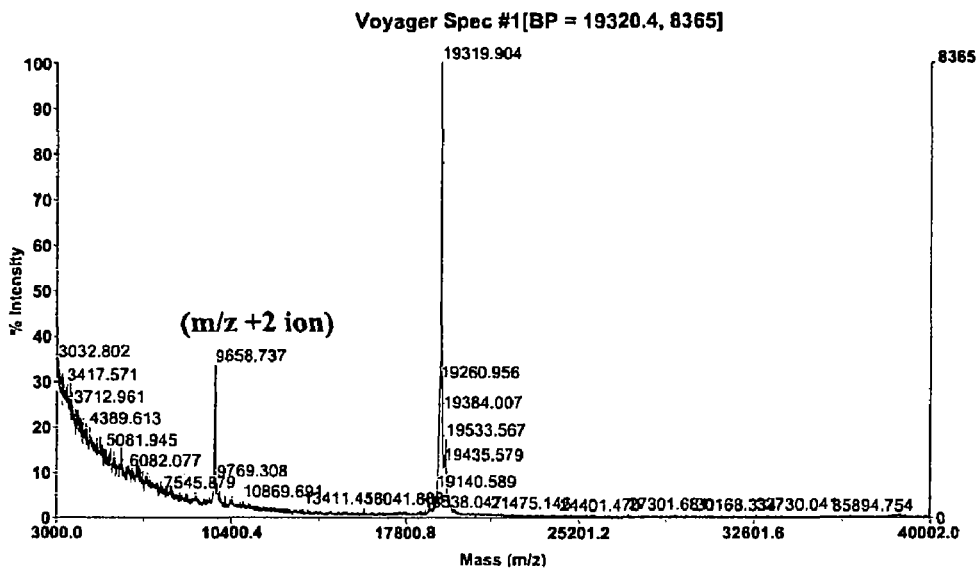
B  Lot ID- CRPV 2.1 LSBC030326-UT
Protein purity (as determined by densitometry) =97.2%
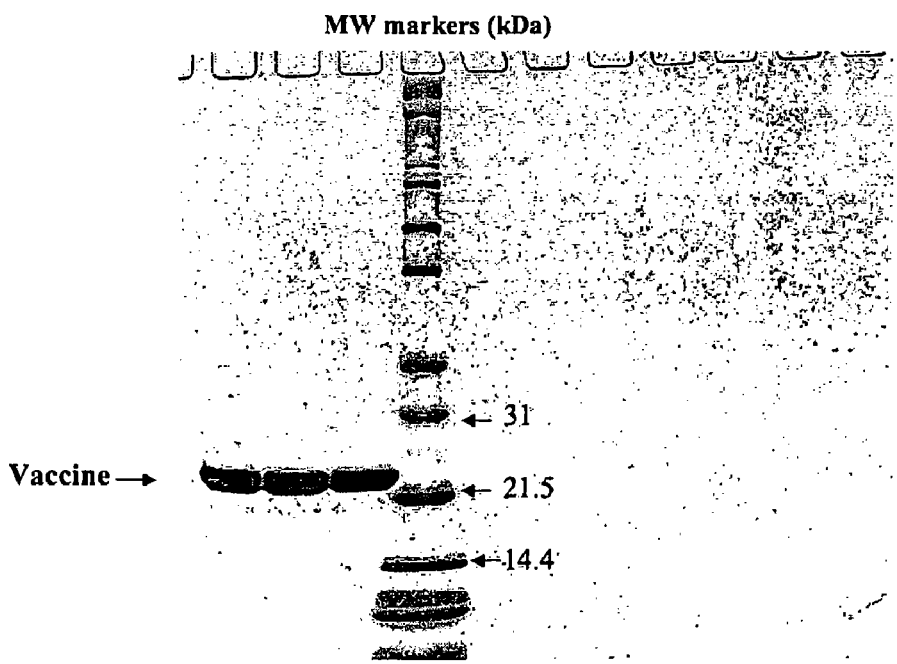

FIG 23
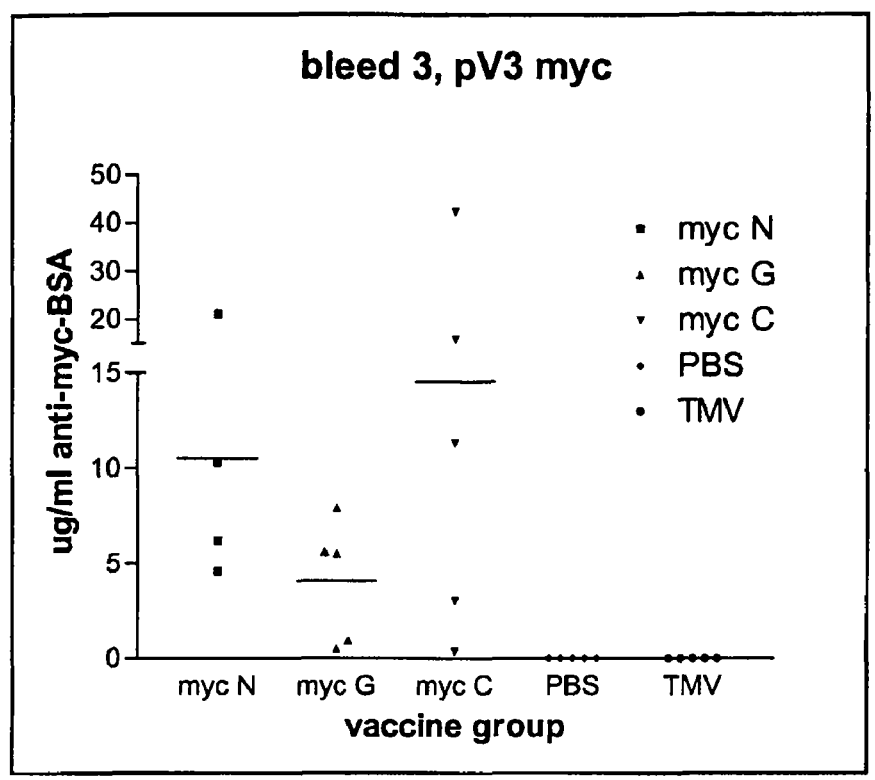
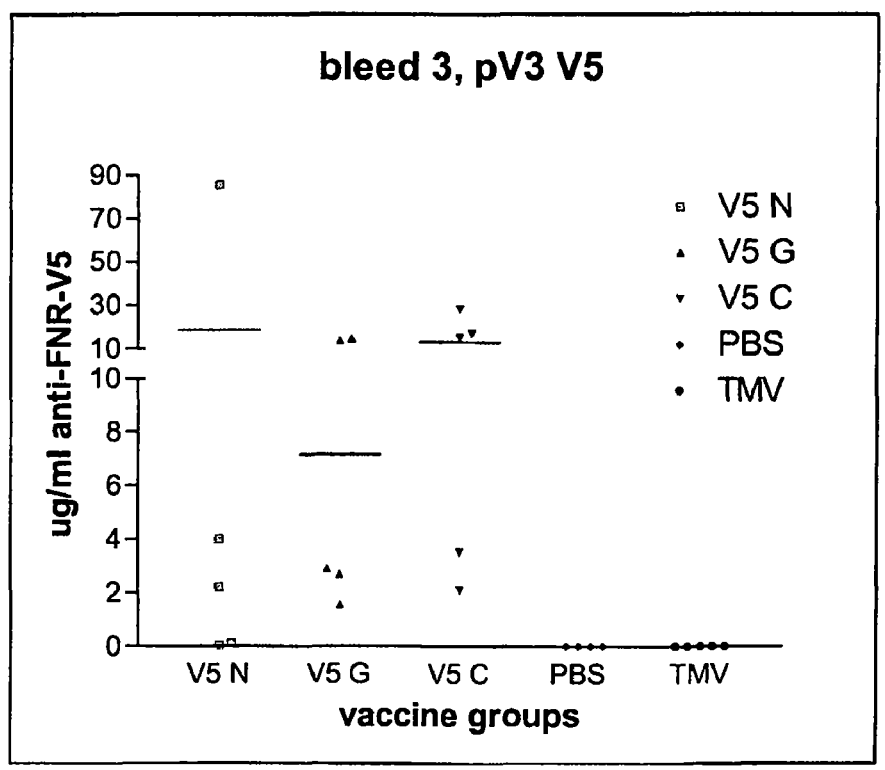

SEQUENCE LISTING

<160> NUMBER OF SEQ ID NOS: 25

<210> SEQ ID NO 1
<211> LENGTH: 15
<212> TYPE: PRT
<213> ORGANISM: Simian Virus 5

<400> SEQUENCE: 1

```
Gly Lys Pro Ile Pro Asn Pro Leu Leu Gly Leu Asp Ser Thr Lys
1               5                   10                  15

<210> SEQ ID NO 2
<211> LENGTH: 10
<212> TYPE: PRT
<213> ORGANISM: Influenza virus

<400> SEQUENCE: 2

Tyr Pro Tyr Asp Val Pro Asp Tyr Ala Lys
1               5                   10

<210> SEQ ID NO 3
<211> LENGTH: 11
<212> TYPE: PRT
<213> ORGANISM: human antibody

<400> SEQUENCE: 3

Glu Gln Lys Leu Ile Ser Glu Glu Asp Leu Lys
1               5                   10

<210> SEQ ID NO 4
<211> LENGTH: 19
<212> TYPE: PRT
<213> ORGANISM: cottontail rabbit papillomavirus

<400> SEQUENCE: 4

Val Gly Pro Leu Asp Ile Val Pro Glu Val Ala Asp Pro Gly Gly Pro
1               5                   10                  15

Thr Leu Val

<210> SEQ ID NO 5
<211> LENGTH: 18
<212> TYPE: PRT
<213> ORGANISM: cottontail rabbit papillomavirus

<400> SEQUENCE: 5

Pro Gly Gly Pro Thr Leu Val Ser Leu His Glu Leu Pro Ala Glu Thr
1               5                   10                  15

Pro Tyr

<210> SEQ ID NO 6
<211> LENGTH: 19
<212> TYPE: PRT
<213> ORGANISM: rabbit oral papillomavirus

<400> SEQUENCE: 6

Val Gly Pro Leu Glu Val Ile Pro Glu Ala Val Asp Pro Ala Gly Ser
1               5                   10                  15

Ser Ile Val

<210> SEQ ID NO 7
<211> LENGTH: 18
<212> TYPE: PRT
<213> ORGANISM: rabbit oral papillomavirus

<400> SEQUENCE: 7

Pro Ala Gly Ser Ser Ile Val Pro Leu Glu Glu Tyr Pro Ala Glu Ile
1               5                   10                  15

Pro Thr

<210> SEQ ID NO 8
<211> LENGTH: 9
```

```
<212> TYPE: PRT
<213> ORGANISM: Human papillomavirus

<400> SEQUENCE: 8

Ala Ala Leu Gln Ala Ile Glu Leu Met
1               5

<210> SEQ ID NO 9
<211> LENGTH: 9
<212> TYPE: PRT
<213> ORGANISM: mouse tyrosinase

<400> SEQUENCE: 9

Ser Val Tyr Asp Phe Phe Val Trp Leu
1               5

<210> SEQ ID NO 10
<211> LENGTH: 8
<212> TYPE: PRT
<213> ORGANISM: mouse

<400> SEQUENCE: 10

Lys Ser Pro Trp Phe Thr Thr Leu
1               5

<210> SEQ ID NO 11
<211> LENGTH: 8
<212> TYPE: PRT
<213> ORGANISM: chicken

<400> SEQUENCE: 11

Ser Ile Ile Asn Phe Glu Lys Leu
1               5

<210> SEQ ID NO 12
<211> LENGTH: 7
<212> TYPE: PRT
<213> ORGANISM: Human immunodeficiency virus

<400> SEQUENCE: 12

Glu Leu Asp Lys Trp Ala Ser
1               5

<210> SEQ ID NO 13
<211> LENGTH: 16
<212> TYPE: PRT
<213> ORGANISM: respiratory syncytial virus

<400> SEQUENCE: 13

Cys Glu Tyr Asn Val Phe His Asn Lys Thr Phe Glu Leu Pro Arg Ala
1               5                   10                  15

<210> SEQ ID NO 14
<211> LENGTH: 17
<212> TYPE: PRT
<213> ORGANISM: tetanus

<400> SEQUENCE: 14

Gln Tyr Ile Lys Ala Asn Ser Lys Phe Ile Gly Ile Thr Glu Leu Lys
1               5                   10                  15

Lys

<210> SEQ ID NO 15
<211> LENGTH: 9
<212> TYPE: PRT
```

-continued

<213> ORGANISM: Human IL1beta

<400> SEQUENCE: 15

Val Gln Gly Glu Glu Ser Asn Asp Lys
1               5

<210> SEQ ID NO 16
<211> LENGTH: 19
<212> TYPE: PRT
<213> ORGANISM: Measles virus

<400> SEQUENCE: 16

Phe Ala Gly Val Val Leu Ala Gly Ala Ala Leu Gly Val Ala Thr Ala
1               5                   10                  15

Ala Gln Ile

<210> SEQ ID NO 17
<211> LENGTH: 7
<212> TYPE: PRT
<213> ORGANISM: human integrin

<400> SEQUENCE: 17

Ser Gly Arg Gly Asp Ser Gly
1               5

<210> SEQ ID NO 18
<211> LENGTH: 6
<212> TYPE: PRT
<213> ORGANISM: human laminin

<400> SEQUENCE: 18

Gly Tyr Ile Gly Ser Arg
1               5

<210> SEQ ID NO 19
<211> LENGTH: 489
<212> TYPE: DNA
<213> ORGANISM: Artificial Sequence
<220> FEATURE:
<223> OTHER INFORMATION: N-terminal Cysteine TMV U1

<400> SEQUENCE: 19

```
atgggatgtg gatcttacag tatcactact ccatctcagt tcgtgttctt gtcatcagcg      60
tgggccgacc caatagagtt aattaattta tgtactaatg ccttaggaaa tcagtttcaa     120
acacaacaag ctcgaactgt cgttcaaaga caattcagtg aggtgtggaa accttcacca     180
caagtaactg ttaggttccc tgacagtgac tttaaggtgt acaggtacaa tgcggtatta     240
gacccgctag tcacagcact gttaggtgca ttcgacacta gaaatagaat aatagaagtt     300
gaaaatcagg cgaaccccac gactgccgaa acgttagatg ctactcgtag agtagacgac     360
gcaacggtgg ccataaggag cgcgataaat aatttaatag tagaattgat cagaggaacc     420
ggatcttata atcggagctc tttcgagagc tcttctggtt tggtttggac ctctggtcct     480
gcaacttga                                                             489
```

<210> SEQ ID NO 20
<211> LENGTH: 489
<212> TYPE: DNA
<213> ORGANISM: Artificial Sequence
<220> FEATURE:
<223> OTHER INFORMATION: N-terminal Lysine TMV U1

<400> SEQUENCE: 20

```
atgggaaaag gatcttacag tatcactact ccatctcagt tcgtgttctt gtcatcagcg    60
tgggccgacc caatagagtt aattaattta tgtactaatg ccttaggaaa tcagtttcaa   120
acacaacaag ctcgaactgt cgttcaaaga caattcagtg aggtgtggaa accttcacca   180
caagtaactg ttaggttccc tgacagtgac tttaaggtgt acaggtacaa tgcggtatta   240
gacccgctag tcacagcact gttaggtgca ttcgacacta gaaatagaat aatagaagtt   300
gaaaatcagg cgaaccccac gactgccgaa acgttagatg ctactcgtag agtagacgac   360
gcaacggtgg ccataaggag cgcgataaat aatttaatag tagaattgat cagaggaacc   420
ggatcttata atcggagctc tttcgagagc tcttctggtt tggtttggac ctctggtcct   480
gcaacttga                                                          489
```

```
<210> SEQ ID NO 21
<211> LENGTH: 15
<212> TYPE: PRT
<213> ORGANISM: Artificial Sequence
<220> FEATURE:
<223> OTHER INFORMATION: Created from Seq ID No. 10 inserted into TMV

<400> SEQUENCE: 21

Ala Met Lys Ser Pro Trp Phe Thr Thr Leu Ala Gly Pro Ala Thr
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Created from Seq ID No: 10 inserted into TMV

<400> SEQUENCE: 22

Ala Met Asp Glu Lys Ser Pro Trp Phe Thr Thr Leu Ala Gly Pro Ala
1               5                   10                  15

Thr

<210> SEQ ID NO 23
<211> LENGTH: 5
<212> TYPE: PRT
<213> ORGANISM: Artificial Sequence
<220> FEATURE:
<223> OTHER INFORMATION: Glycine Cysteine linker

<400> SEQUENCE: 23

Gly Gly Cys Gly Gly
1               5

<210> SEQ ID NO 24
<211> LENGTH: 162
<212> TYPE: PRT
<213> ORGANISM: Artificial Sequence
<220> FEATURE:
<223> OTHER INFORMATION: N-terminal Cysteine TMV U1

<400> SEQUENCE: 24

Met Gly Cys Gly Ser Tyr Ser Ile Thr Thr Pro Ser Gln Phe Val Phe
1               5                   10                  15

Leu Ser Ser Ala Trp Ala Asp Pro Ile Glu Leu Ile Asn Leu Cys Thr
            20                  25                  30

Asn Ala Leu Gly Asn Gln Phe Gln Thr Gln Gln Ala Arg Thr Val Val
        35                  40                  45

Gln Arg Gln Phe Ser Glu Val Trp Lys Pro Ser Pro Gln Val Thr Val
    50                  55                  60
```

Arg Phe Pro Asp Ser Asp Phe Lys Val Tyr Arg Tyr Asn Ala Val Leu
65                  70                  75                  80

Asp Pro Leu Val Thr Ala Leu Leu Gly Ala Phe Asp Thr Arg Asn Arg
            85                  90                  95

Ile Ile Glu Val Glu Asn Gln Ala Asn Pro Thr Thr Ala Glu Thr Leu
            100                 105                 110

Asp Ala Thr Arg Arg Val Asp Asp Ala Thr Val Ala Ile Arg Ser Ala
            115                 120                 125

Ile Asn Asn Leu Ile Val Glu Leu Ile Arg Gly Thr Gly Ser Tyr Asn
            130                 135                 140

Arg Ser Ser Phe Glu Ser Ser Ser Gly Leu Val Trp Thr Ser Gly Pro
145                 150                 155                 160

Ala Thr

<210> SEQ ID NO 25
<211> LENGTH: 162
<212> TYPE: PRT
<213> ORGANISM: Artificial Sequence
<220> FEATURE:
<223> OTHER INFORMATION: N-terminal Lysine TMV U1

<400> SEQUENCE: 25

Met Gly Lys Gly Ser Tyr Ser Ile Thr Thr Pro Ser Gln Phe Val Phe
1               5                   10                  15

Leu Ser Ser Ala Trp Ala Asp Pro Ile Glu Leu Ile Asn Leu Cys Thr
            20                  25                  30

Asn Ala Leu Gly Asn Gln Phe Gln Thr Gln Ala Arg Thr Val Val
            35                  40                  45

Gln Arg Gln Phe Ser Glu Val Trp Lys Pro Ser Pro Gln Val Thr Val
    50                  55                  60

Arg Phe Pro Asp Ser Asp Phe Lys Val Tyr Arg Tyr Asn Ala Val Leu
65                  70                  75                  80

Asp Pro Leu Val Thr Ala Leu Leu Gly Ala Phe Asp Thr Arg Asn Arg
            85                  90                  95

Ile Ile Glu Val Glu Asn Gln Ala Asn Pro Thr Thr Ala Glu Thr Leu
            100                 105                 110

Asp Ala Thr Arg Arg Val Asp Asp Ala Thr Val Ala Ile Arg Ser Ala
            115                 120                 125

Ile Asn Asn Leu Ile Val Glu Leu Ile Arg Gly Thr Gly Ser Tyr Asn
            130                 135                 140

Arg Ser Ser Phe Glu Ser Ser Ser Gly Leu Val Trp Thr Ser Gly Pro
145                 150                 155                 160

Ala Thr

FLEXIBLE VACCINE ASSEMBLY AND VACCINE DELIVERY PLATFORM

This application is a continuation of U.S. patent application Ser. No. 10/457,082, filed Jun. 6, 2003, now abandoned which claims the benefit of U.S. Provisional Application No. 60/386,921, filed Jun. 7, 2002, which is incorporated herein by reference in its entirety.

This invention was made with United States Government Support under cooperative agreement number 70NANB2H3048 awarded by the National Institute of Standards and Technology.

FIELD OF THE INVENTION

The invention relates to a novel vaccine platform that includes a reassembled virus constructed from one or more subunits, each subunit containing a different peptide or nucleic acid moiety added by genetic fusion or in vitro conjugation such that each subunit incorporates a target therapeutic agent. The invention further relates to a method for assembling RNA molecules in vitro for delivery and expression in eukaryotic cells. In particular, the invention provides for proteins, molecules and nucleic acid sequences necessary for the packaging of RNA molecules for delivery and expression in a eukaryotic cell. The packaged RNA molecules of the invention are capable of delivery to a wide range of eukaryotic cells. The packaged RNA molecules may also be targeted to specific eukaryotic cells. The invention further includes a delivery platform where the above described reassembled viruses or virus-like particles (VLPs), RNA vaccines are used to induce either cellular or humoral immunity, or both simultaneously, by the synergistic action of peptide fusions to the virus or VLP structure and the encoded proteins of the RNA.

BACKGROUND OF THE INVENTION

To date, most traditional vaccines have been composed of live-attenuated or inactivated whole pathogen preparations. Generation of these sorts of vaccines is limited by the requirement for long and intensive basic research and development. Reliable production and scale-up technologies for live-attenuated or inactivated vaccines would be almost impossible to develop at short notice. There is, therefore, a need for the development of a safe, robust and broadly-useful technology that is suitable for the production of vaccines against unanticipated infectious disease threats. Vaccines developed from plant-virus-pathogen chimera's may provide a method to rapidly produce vaccines that can be used to prevent or treat a number of known or emerging disease threats.

Controlling immune responses to pathogens and tumor cells has been the focus of immunology, cell biology and pharmaceutical development for several decades. Much has been learned about the complexity of immune cells and the patterns and effect of cytokine expression in response to pathogen challenge, and vaccine administration. One key aspect of this work has been the identification of two major arms of the immune response, the Th1 response, which is largely cellular, and the Th2 response, which is predominantly humoral. The two types of immune responses are mounted in response to how foreign antigens are presented to the immune system, what cytokines are expressed by presenting cells and what types of immune cells are activated. Th1 responses result in cytotoxic immune cell function and production of neutralizing antibodies of a different subtype than observed with Th2 responses. While some pathogens can be susceptible to Th2 responses, the Th1 response is key to mounting an effective response to both pathogen and tumor cells. However, both pathogens and tumor cells have developed strategies to avoid immune surveillance, bypassing mechanisms that are essential to Th1 immunity.

A key goal in vaccine development is to direct Th1 type immunity, in addition to Th2 humoral responses, upon vaccine administration to the host. By using an attenuated cowpox virus, Jenner unknowingly took advantage of the powerful activation of Th1 pathway to prevent smallpox infections. Since his time, most pathogen vaccines have been killed or attenuated, which have generally shown good success in controlling pathogen morbidity and viral spread. However, two aspects of recent vaccine development have led to growing concerns for live or attenuated viral vaccines. The use of an attenuated or killed virus to treat human immunodeficiency virus (HIV) is impractical for several reasons. Occupational safety concerns, low yield of attenuated virus, and the threat of viral mutation or escape are serious drawback to both vaccine development and public acceptance. In other cases, as observed with measles virus and respiratory syncytial virus (RSV), unpredictable and severe adverse events are associated with whole virus immunization. Therefore, much research has focused on "subunit" vaccines, which are composed of pathogen protein(s) or peptides that are generally targeted by the host immune response for protective immunity (*Vaccines*, $3^{rd}$ ed 1999, Plotkin and Orenstein, Philadelphia Pa., Saunders Co). Unfortunately, protein subunit vaccines don't often elicit strong Th1 responses by themselves, and DNA subunit vaccines often fail to elicit antibodies. In most cases both antibodies and CTL responses are necessary in controlling pathogenesis or disease progression.

Two new types of vaccines have been created to overcome the deficiencies of current subunit vaccines. Non-pathogenic viruses have been genetically modified to encode immunogenic subunit proteins of a pathogen, thus taking advantage of the Th1 immune response to viral antigen presentation. Strong Th1 type immune responses have been demonstrated for many pathogen and self-antigens using adenovirus, vaccinia, fowlpox and alphavirus delivery systems (Walther and Stein. 2000 Drugs 60, 249). However, these "first generation" viral delivery systems encountered problems due to the vector immunogenicity, which precluded their subsequent use in booster immunizations. Viral priming followed by either protein or DNA boosting has been successful, but this approach requires the manufacture of at least two agents for a single vaccine. The large-scale manufacture of DNA and/or protein for these vaccines has encountered both technical and financial challenges.

A second strategy takes advantage of the self-assembly of viral coat proteins into virus like particles (VLPs), which by themselves stimulate strong Th1 antigen responses (Schiller and Lowy. 2001 Expert Opin Biol Ther. 1, 571). VLPs constructed from arrayed viral coat have been shown to be effective in stimulating both neutralizing antibody and cytotoxic T lymphocyte (CTL) responses. Viral coat proteins are also effective carriers of antigens through fusion to the external solvent-exposed residues, usually by genetic fusion (Pogue et al. 2002 Ann Rev Phyto Path 40, 3; Da Silva. 1999 Curr Opin Mol Ther 1, 82). Though promising, VLP technology also has drawbacks. Production is again limiting, and often fusion of a heterologous antigen to the coat reduces VLP yield, solubility, or prevents self-assembly. In addition, immune clearance, the same mechanism that limits whole virus boosting, also limits the use of VLPs. Clearly, there is a need for a cost effective viral coat antigen delivery system that overcomes the limitations of both whole virus and VLP technology for vaccine delivery. The properties of this system would include all the benefits of boosting Th1 responses via a virus-like antigen presentation to the immune system without pathogenicity, flexibility to rotate the VLP backbone to which the antigen is fused, generation of and control of immunogenicity, high yield and low cost.

Applicant and others have shown that coat proteins from plant viruses have all the immunologic presentation properties of mammalian virus coat, but without pathogenicity. A large number of positive (+) strand RNA plant viruses, including Tobacco Mosaic Virus (TMV), type member of the tobamovirus family, have been cloned and manipulated in vitro to express heterologous gene products in plants as well as to display biologically relevant peptides on its virion surface. A unique property of TMV virions is their ability to be disassociated to form monomers and self assemble into VLPs using a RNA scaffold. Plant coat proteins, including TMV, engineered to display foreign epitopes have been shown to promote functional immunity to both self-antigens (Savelyeva N 2001 Nat Biotechnol 19 760) and various pathogens (Pogue et al. 2002 Ann Rev Phyto Path 40, 3).

Essential for the encapsidation of the viral genomic RNA molecule into an infectious particle is the presence of a sequence element referred to as the origin of assembly (OAS). The TMV OAS is located approximately 1 Kb from the 3' end of the viral genome and consists of a 440 nucleotide sequence that is predicted to form three hairpin stem-loop structures (Turner and Butler, 1986). The viral coat protein disks initially bind to loop 1 during viral assembly. In vitro packaging assays using mutual assembly origin transcripts have defined the 75 nucleotides comprising loop 1 as necessary and sufficient for encapsidation of foreign or viral RNA sequences (Turner et al., 1988). In vitro reconstitution studies have shown that preparations of purified coat protein, derived from virions from infected plant cells, are able to assemble into helical structures with TMV RNA at pH 7.0, resulting in assembly of TMV-like viral particles containing RNA (Fraenkel-Conrat and Williams, 1955). Furthermore, it has been shown that foreign chimeric RNA molecules containing OAS sequences, transcribed in vitro using SP6 or T7 RNA polymerase, may be assembled in vitro into pseudovirus particles (Sleat et al., 1986).

The cloning and sequencing of the viral coat proteins responsible for encapsidation has led to the insertion of these genes into bacterial expression vectors in, for example, E. coli (Shire et al., 1990). However, in vitro assembly with recombinant E. coli viral coat proteins results in a decreased reconstitution rate relative to native coat protein produced in plants (Shire et al., 1990). U.S. Pat. No. 5,443,969 attempts to overcome this deficiency in E. coli by packaging RNA sequences containing a TMV-OAS in vivo in E. coli, instead of in vitro. However, introduction of the encapsidated viral vectors into hosts outside of plants is problematic. The lack of acetylation of the TMV coat protein in E. coli results in poorly efficient encapsidation of non-capped RNAs. These RNAs are poorly translated in eukaryotic cells due to the lack of the cap structure. Further, the yields of recombinant TMV products in E. coli are very poor and not commercially feasible.

The process of intracellular delivery of genetic material for therapeutic purposes by either correcting an existing abnormality or providing cells with a new function is the basis behind gene therapy (Drew and Martin, 1999), and for DNA immunizations. Practically speaking, nucleic acid immunization technologies present an attractive front-line defense against new pathogens: there is probably no other system that can compete as the first line in a rapid-response subunit vaccine strategy. However, conventional DNA vaccines suffer from a number of significant drawbacks that makes reliance on this technology alone unwise. Most significantly, the dose of DNA required to stimulate an effective immune responses is very high, with the implication that production of significant quantities for large scale immunization will be challenging. DNA and RNA vaccines are generally capable of promoting good Th1 type cytotoxic T cell responses, which are essential for elimination of non-cytopathic pathogens. However, with few exceptions, the antibody response induced by DNA vaccines is poor. Hence, although nucleic acid vaccines are attractive from the prospective that production can be very rapid, ideally an initial DNA or RNA vaccination should be followed by a booster vaccination, preferably with protein, to induce efficient antibody production and more complete protection against pathogen challenge. The current invention addresses the issues raised above by introducing a novel and flexible vaccine delivery platform

SUMMARY OF THE INVENTION

The present invention includes several unique solutions that address current limitations of VLP technology, while retaining all the positive characteristics of a successful VLP antigen scaffold. Applicant presents a method for generating VLP vaccines in adaptable, predictable, stable and scaleable manners. This work is highly innovative, and there is continuing development. The method includes generating multi-valent vaccines where different vaccine protein moieties are fused to the surface of a single VLP structure conferring a multi-functional effect—the availability of immune peptides (protein elements stimulating protective immunity) and peptides that either modulate the host immune response or facilitate efficient immune cell recognition or processing. The proposed vaccines will be also bi-functional, where the protein elements of the VLP, with or without a peptide fusion or series of fusions, encapsidate a modified RNA moiety. The modified RNA can carry an mRNA of interest and that protected RNA can then be used to carry nucleic acid content, along with protein, into an immune cell that takes up the vaccine. The RNA constituents works synergistically to generate strong, lasting immunological responses by encoding either an intact pathogen or oncology antigen, proteins that stimulate host immune responses or proteins that modulate either a type Th1 or Th2 immune response to the vaccine. The method alleviates problems associated with other VLP systems by having robust production potential, improved cellular uptake, and multi-epitope valency. A selection of structurally similar, yet immunologically distinct VLP carriers allows rotation of the coat backbone for prime-boost strategies that have proven unworkable in other VLP systems.

Vaccination with bi-functional RNAs presents an alternative to DNA vaccination, with some distinct advantages. In the first instance, there is little concern that an RNA-based vaccine could cause oncogenesis because it cannot incorporate into or transform the genome. Secondly, there is good evidence that one could deliver an RNA vaccine derived from an RNA virus (such as an alphavirus) as a safe self-amplifying vaccine vector. Alphavirus replicons are cytolytic for cells, and thus the replicating RNA vaccine is intrinsically transient and self-eliminating. Alphavirus "replicon" vaccines cause powerful immune responses—both antibody and cell-mediated—associated with both increases in the amount of antigen produced as well as the production of inflammatory cytokines induced by intracellular accumulation of the viral dsRNA replicative intermediate. These features indicate that the dosage of replicative RNA required for induction of effective immune responses would be orders of magnitude lower than that required by DNA immunization. However, the major drawback associated with naked RNA vaccines is the notoriously labile nature of the nucleic acid: this severely limits the application of RNA vaccines for mass immunizations.

Alphavirus replicon vaccines are currently delivered either as naked RNA transcribed in vitro, packaged in alphavirus-like particles (replicon particles), or as plasmids containing infectious cDNAs, driven by the cytomegalovirus immediate early promoter (CMV promoter). Replicon particles are very efficient as vehicles for carrying the replicon RNAs into cells, but production is complicated, inefficient and unreliable. An efficient packaging and RNA stabilization technology is therefore required to protect alphavirus-based RNA vaccines from degradation. Two viable options present themselves: (1) to deliver recombinant alphavirus constructs as infectious cDNA plasmids; (2) to package alphavirus RNA transcribed in vitro such that it is protected from nucleases and has good stability and storage properties. An approach for the latter option is presented below.

The inventors employ as a VLP carrier the well-characterized plant virus, tobacco mosaic virus (TMV), and exploit its unique abilities to reconstitute VLP structures in vitro onto various heterologous RNA sequences.

By introducing a cysteine in the solvent exposed sequences of TMV coat, we can introduce and fuse foreign antigen epitopes ex-vivo. Epitope sequences that are not amenable to in vitro synthesis will be fused in-frame genetically to the TMV coat protein. TMV VLPs will be reassembled in vitro decorated with a single epitope (monovalent), or with a collection of different epitopes (multivalent), derived from in vitro conjugation or expressed from a genetic fusion.

As a scaffold for reassembly, the present invention includes using an RNA that encodes a protein that will enhance vaccine potency, thereby creating a bi-functional antigen delivery system that derives its activity from both protein and nucleic acid. The RNA can also incorporate an alphavirus replicon to augment translation. Essential for the encapsidation of the RNA molecule by the TMV coat protein, to generate an RNA-containing VLP, is the presence of the 75 nucleotide sequence comprising loop 1 of the origin of assembly (OAS). By combining this 75 nucleotide sequence with foreign sequences encoding protein(s) or peptide(s) of therapeutic interest, the RNA molecule can function as an effective scaffold for the generation of a TMV-like VLP. The RNA can encode any number of immunomodulating factors (e.g. IL4, IL1β or IFNγ) that ensure a highly successful immune response to the vaccine, and help generate either protective or therapeutic immunity to the pathogen, or deliver inhibitory RNA signal (RNAi) for targeted gene inhibition. This VLP strategy can be applied to effectively target immune cells and stimulate Th1 type responses.

An important requirement to inducing a Th1 type immune response is getting VLPs into cells for processing and antigen presentation. Peptides with known cell targeting have been identified (Samuel O., Shai, Y., 2001 Bichem. 40, 1340; Magnusson et al. 2001 J. Virol. 75 7280; Bushkin-Harav et al. 1998 FEBS L. 424 243) and can be tested in vitro by direct examination of cell entry, and in vivo for augmented antigen presentation by examining the type and speed of immune response to target antigens. Targeting and fusion peptides will be tested for their ability to augment cellular uptake of TMV, as well as their ability to deliver encapsidated RNA in vitro and in vivo.

A common method to improving vaccination is to co-administer an adjuvant or a specific T-helper peptide to stimulate T-cell help. CpG DNA has been shown to be an easily administered adjuvant that improves Th1 type immune responses when co-administered with an appropriate vaccine (Krieg. 2000 Vaccine 19, 618). Most CpG DNA adjuvants have been given mixed with the vaccine and administered subcutaneously (s.c.), although the single strand thiolated DNA can also be fused to a protein carrier through SPDP conjugation chemistry. Also, several universal T-helper peptides have been identified (Kulkarni, A. B., et al., 1995 J. Virol. 69,1261; Panina-Bordignon, 1989 Eu. J. Imm. 19, 2237; Boraschi, 1988 J Exp Med. 168,675; Weiner, G. et al., 1997 Proc. Nat. Acad. Sci 94 10833). Immunostimulatory peptides, usually fragments of cytokines, have also been identified that direct Th1 type immunity after vaccination in combination with pathogen or self-antigen peptides or subunit vaccines (IL1β, Boraschi, 1988 J Exp Med. 168,675). Coat fusions containing T-helper or adjuvant peptides or CpG DNA oligo will be used to augment the immunogenicity of co-expressed peptides, or encapsidated RNA.

Lastly, it is well established that cytokines play an important role in determining which arm of the immune system is activated after vaccine delivery. Interleukin 4 (IL4) has been implicated in directing Th2 type immune responses and interferon gamma (IFNγ) is an important contributor to Th1 responses (Spellberg and Edwards. 2001 Clin Infect Dis 32, 76). By introducing IL4 and IFNγ RNA into cells by encapsidation into a TMV VLP, we may be able to influence the type of immune response that is generated. Applicant can test both antibody isotype responses to antigen, which are a reflection of Th1 or Th2 antigen presentation, as well as assess CTL responses that are primarily a consequence of Th1 immunity.

Cell fusion peptides, T-help, adjuvants, pathogen antigens, tumor antigens and encapsidated cytokine RNA will be tested systematically in combination with antigens from Papillomavirus and melanoma murine disease models. Immunogencity and challenge models will establish incremental improvements over vaccination with single peptides, and define the best peptide/RNA combinations for generating Th1 or Th2 immune responses.

The availability of such a flexible and effective vaccine platform provides opportunities to apply non-live vaccines for humans and livestock thus reducing side effects and increasing effectiveness. New vistas of medical practice, including applications for breaking self-tolerance and driving immune responses against weak antigens, may be opened by the synergistic and high specific-activity of the disclosed vaccine platform.

The invention relates to a method where a specified virus, such as a tobacco mosaic virus (TMV), is disrupted into a plurality of subunits. Each subunit contains a genetically fused peptide or is subjected to a conjugation reaction in order to attach a predetermined epitope, peptide or nucleotide thereto. A plurality of subunits are processed in this manner to produce a plurality of subunit groups, where one subunit group has attached thereto a predetermined peptide; another subunit group has a second peptide; another subunit has a predetermined epitope attached there to; and another subunit group has a nucleotide attached thereto, and so on, for as many subunit groups necessary to provide the building blocks for a plurality of virus vaccines.

An alternative strategy is to employ TMV RNA modified to initiate internal ribosomal entry by introducing specific sequences known to cause such an effect. These internal ribosomal entry sites (IRES) are effective in causing internal translation products from a polycystronic RNA in mammalian cells (Yang et al., J Virol 1989 63(4):1651-60). Introduction of an IRES into a TMV genome in frame with an RNA encoding either a full length gene product or immunostimulatory cytokine or other kind of immunomodulatory protein allows for translation of that protein. Because these IRES are introduced into non-replicating RNA, the amount of TMV and proportional transcript taken up by a cell after vaccination is conceivably lower than with a self replicating RNA such as encoded by an alphavirus replicon, but the level of translation product should be sufficient to induce the correct response.

The present invention includes research and development of technological solutions to help the USA to produce and supply effective vaccine reagents in response to unanticipated pathogen threats. Applicant specifically addresses issues that limit bio-defense application of nucleic acid vaccines: poor environmental stability and high dosage requirements. In addressing these issues, we will draw upon the core of knowledge that the inventors possesses in the field of positive stranded RNA viruses and their applications in biotechnology to develop a set of molecular tools to improve nucleic acid vaccines. Applicant will also demonstrate our capacity to produce protein subunit vaccines that will-provide effective antibody responses. Production of protein subunit vaccines is inherently slower than nucleic acid vaccines and so, practically, will only be available within a delayed period following encounter with a new pathogen threat. However, the inventor's non-transgenic plant-based vaccine expression platform (GENEWARE®) has the capability to express a variety of proteins, including virus-like particles (VLP)—known to be potent inducers of antibodies in vaccinated individuals—rapidly. Applicant has recently used a modified TMV expression vector to produce 16 different human therapeutic vaccines in tobacco plants, and have shown excellent safety in a Phase I clinical trial (BB-IND #9283). Unlike other competing technologies, GENEWARE® does not require specialized fermentation facilities, and uses the efficient, rapid protein production strategy of the plant virus TMV to harness plant protein production machinery to produce vaccine proteins. A typical harvest time, post inoculation is less than 21 days. Since the same virus is used from pilot testing to large-scale manufacturing, there is little or no transition time between validation and manufacturing scale up. Most of the delay in delivery of vaccines via GENEWARE® technology would be in the growth of plants, and establishment of antigen-specific purification protocols. These aspects of the technology result in a low cost of production for plant-derived VLP vaccines.

LIST OF FIGURES

FIG. 1 is a flow diagram outlining the standard methods for the generation of multivalent vaccines via chemical fusions FIG. 2 is a flow diagram outlining methods to generate multivalent TMV-based vaccines via chemical fusions that can be bifunctional through the use of a translatable RNA species as a scaffold FIG. 3 is a flow diagram outlining the standard methods for the generation of multivalent vaccines via genetic fusions FIG. 4 is a flow diagram outlining methods to generate multivalent TMV-based vaccines via genetic fusions that can be bifunctional through the use of a translatable RNA species as a scaffold FIG. 5 is a rendering of TMV virion disassembly and in vitro virion reassembly, showing from left to right: an electron micrograph of a single TMV virion; space filling models of an individual TMV coat protein, with schematic placement of surface exposed N—(N) and C—(C) terminal domains and surface exposed loop (SL); space filling models of 20S disk subunits; and a reassembled VLP surrounding RNA.

Figure 6:
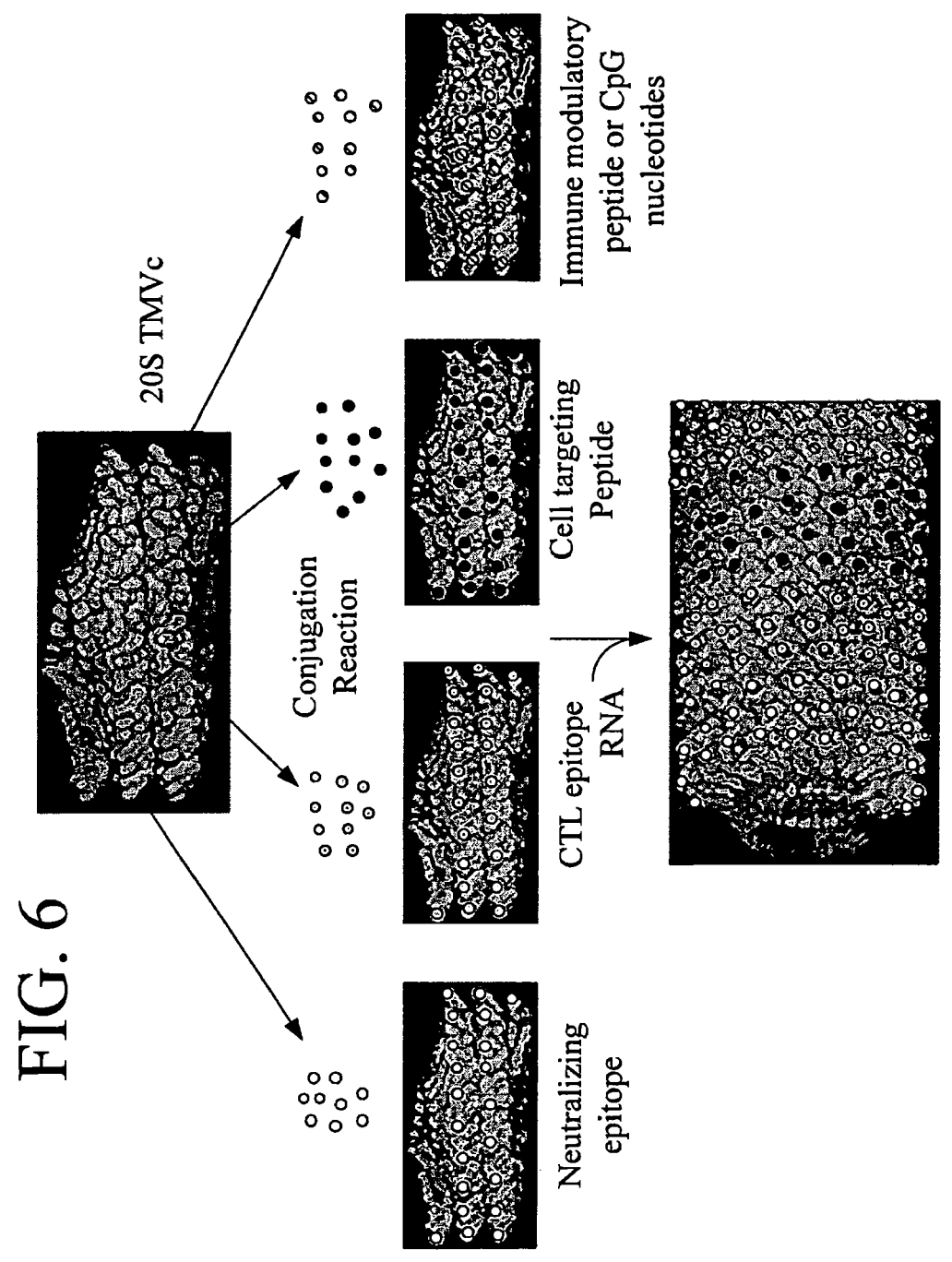

FIG. 6 is a schematic of in vitro conjugation, or molecular fusion, of heterologous peptides of various biological functionalities to modified TMV 20S subunits and reassembly of heteropolymeric (multiple peptide display) VLP surrounding bioactive RNA.

FIG. 7 shows the expression levels of TMV-HA peptide fusions at different insertion sites in TMV U1 coat protein. N. Benthamiana plants (21 days post sow) were inoculated with encapsidated RNA with a mild abrasive and approximately 200 µg tissue was harvested 9 to 10 days post infection. Samples were ground in 300 µl acetate buffer pH 5, and insoluble material was pelleted by centrifugation. Total plant proteins were harvested by grinding 100 µg tissue in 100 µl SDS-PAGE buffer. The soluble supernatant was removed and then the pellet was resuspended in 200 µl Tris buffer pH 7.5 for a final pH extraction at pH7. 10 µl of each sample was then separated by 10-20% SDS-PAGE, stained in Coomassie brilliant blue and destained before photographing. HA N accumulates as a pH5 insoluble pH7 soluble coat fusion at approximately 19 kD (arrow). HA Loop is expressed, but insoluble (present in total SDS grind but not soluble fractions 5 or 7). HA GPAT is expressed and soluble at pH5 but is cleaved, and only partially cleaved at pH7. Ha C is expressed and is insoluble at pH5 and soluble at pH7 with minor cleavage products visible. 5: Acetate buffer pH5; 7: Tris buffer pH 7; S: SDS PAGE buffer total tissue grind.

FIG. 8 shows TMV proteins that were harvested from plants infected with p15eTMV or p15e DE TMV after signs of infection were evident. 20 mg leaf discs were then processed in Acetate buffer A: 50 mM Na-acetate (pH 5.0)/5 mM EDTA, then the insoluble material was resuspended in tris buffer T: 50 mM TRIS (pH 7.5)/10 mM EDTA, and material was compared to processing in SDS page buffer S: 78 mM TRIS (7.0)/10% (w/v) sodium dodecyl sulfate/0.05% bromophenyl blue/6.25% Glycerol/10% β-mercaptoethanol, for total protein analysis. Materials were then separated by SDS-PAGE, and visualized by Coomassie staining. The control was U1: wild type coat protein of tobacco mosaic virus strain U1, M: protein molecular weight standard.

FIG. 9A (1) shows the nucleic acid sequence (Seq ID No: 19) and amino acid translation (Seq ID No: 24) for N terminal Cysteine TMV U1. Alternatively the cysteine can be incorporated into other tobamovirus coats and at other positions within the coat protein, e.g., 60s loop, C terminus, read through position. (2) Composition for N terminal Lysine TMV U1 nucleic acid sequence (Seq ID No: 20), and amino acid translation (Seq ID No: 25). Alternatively the lysine can be incorporated into other tobamovirus coats and at other positions within the coat protein, e.g., 60s loop, C terminus, read through position.

FIG. 9B shows chemical conjugation to cysteine containing TMV coat protein by glutaraldehyde. 1.0 mg of peptide was mixed with 1.0 mg of Cyst-N TMV (C—N), in a volume of 1 ml, and a 20 µl sample was removed for T=0. This sample was added to 20 µl of water and 40 µl of 2× PAGE buffer, and immediately boiled. (The water in T=0 equalizes its concentration with that of T=4 which has added glutaraldehyde.) Glutaraldehyde was added to the reaction to a final concentration of 1%, in a final volume of 2 ml. The reaction was allowed to proceed for 4 hours at room temperature, with constant rotation. After 4 hours, a sample was removed for a T=4 time point, added to an equal volume of 2× PAGE buffer and immediately boiled. 8 µl (2 µg peptide & 2 µg carrier) of each time point was loaded on a gel for Western transfer to nitrocellulose, and 16 µl (4 µg peptide & 4 µg carrier) of each time point was loaded on a gel for Coomassie staining.

FIG. 10 shows transmission electron micrograph (TEM) images of TMV wild-type and myc or V5 N terminal fusion virus. TMV, TMV-myc-N or TMV-V5-N were coated onto 400-mesh carbon-coated copper grids at 20 to 80 µg/ml.

Samples were then negatively stained with 1% phosphotungstic acid, dried and stored at RT until visualized using a Philips CM120 TEM, at 37,000× magnification. The bar represents 130 nm.

FIG. 11(A) shows a flow diagram for the purification of TMV U1 virus from infected plant material. (B) SDS-PAGE analysis (10-20% tris-glycine gel) for the isolation of TMV U1 from infected *N tabacum* MD609 plants. Since the majority of the virus partitioned into the S1 supernatant the S2 supernatant was not processed. GJ, green juice; S1, supernatant S1; S1 PEG1, resuspended virus from the first PEG precipitation; S1 PEG2, resuspended virus from the second PEG precipitation.

FIG. 12 shows an SDS gel (10-20% tris glycine) illustrating the effect of salt on the virus partitioning between the S1 and S2 process streams for the Cysteine N coat protein fusion. GJ, initial green juice; S1, S1 process stream; S2, S2 process stream.

FIG. 15(A) shows the ultraviolet absorption spectrum for TMV U1 coat protein at pH 8.0. (B to D) Treatment of Myc N coat protein with DEAE Sepharose to remove contaminating residual RNA. (B) and (C) Comparison of the ultraviolet absorbance spectrum before and after DEAE resin treatment. (D) Agarose gel electrophoresis to track contaminating RNA. Following binding of the starting coat (L) to the DEAE resin, the coat protein was eluted with 50 mM NaCl (E50) yielding a preparation free from RNA. 500 mM NaCl was required to elute the RNA from the resin (E500). FT represents the resin flow through.

Figure 16:
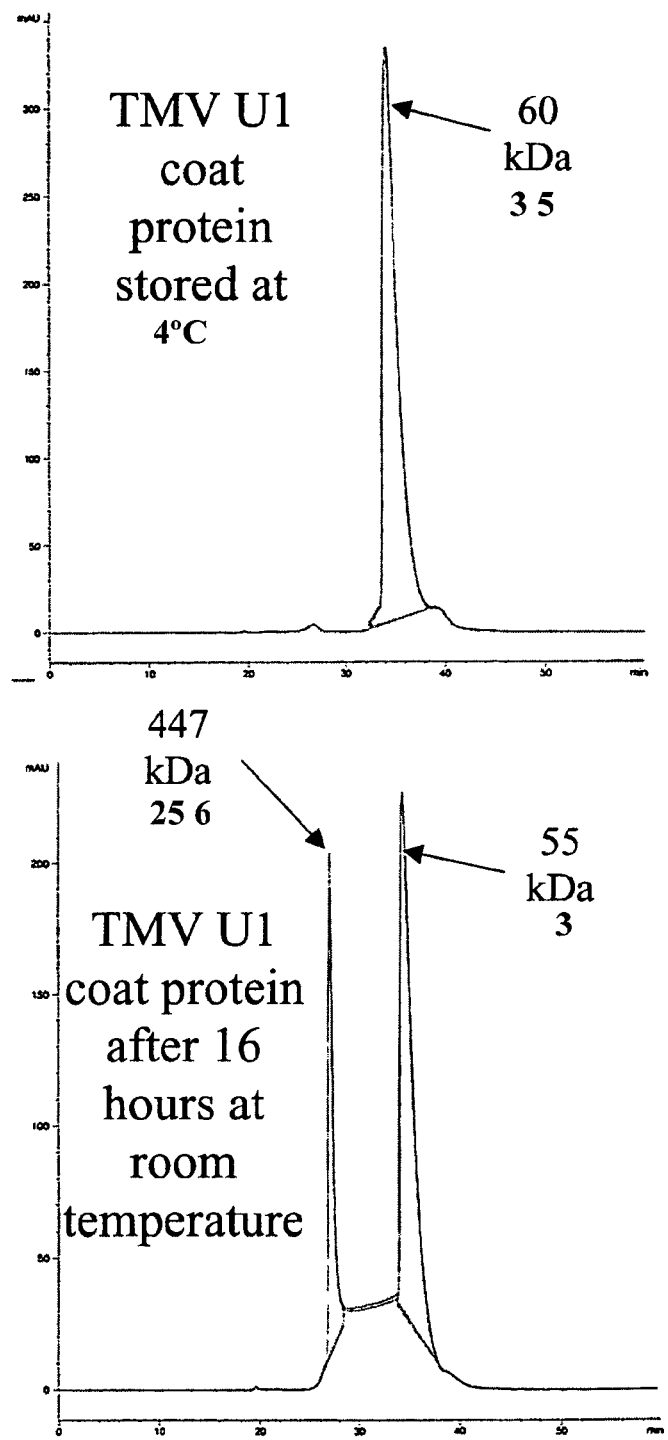

FIG. 16 shows the change in the chromatogram for TMV U1 coat protein, analyzed by size exclusion chromatography, before and after incubation at room temperature. (A) Chromatogram profile for coat protein stored at 4° C. (B) Chromatogram profile for coat protein following storage for 16 hours at room temperature. A YMC-Pack Diol-300 column (5 μm bead; pore size, 30 nm) was employed and the flow rate was 0.5 ml/min. The buffer employed was 0.1 M phosphate, pH 7.0 at either 4° C. or room temperature, based on the temperature of the sample injected.

FIG. 17(A) Shows the kinetics of virion reconstitution from viral RNA plus the U1 coat protein, which were followed by the increase in solution turbidity at 310 nm. This is approximately proportional to the average rod length. TMV virus, at a molarity equivalent to that of the starting RNA, was employed to indicate the optical density of a fully reconstituted in vitro encapsidation. (1) Standard IVE conditions; 0.1 M sodium phosphate, pH 7.2. (2) 0.1 M phosphate pH 7.2 with RNasin at 0.4 U/μl. (3) 0.1 M sodium pyrophosphate, pH 7.2. (B) Agarose gel electrophoresis of final reassembly reactions to assess RNA integrity. RNA Cntrl, RNA lacking coat protein; PO4, phosphate buffered reassembly reaction; Pyro PO4, pyrophosphate buffered reassembly reaction; PO4 RNasin, phosphate buffered reassembly reaction containing RNasin.

Figure 18:
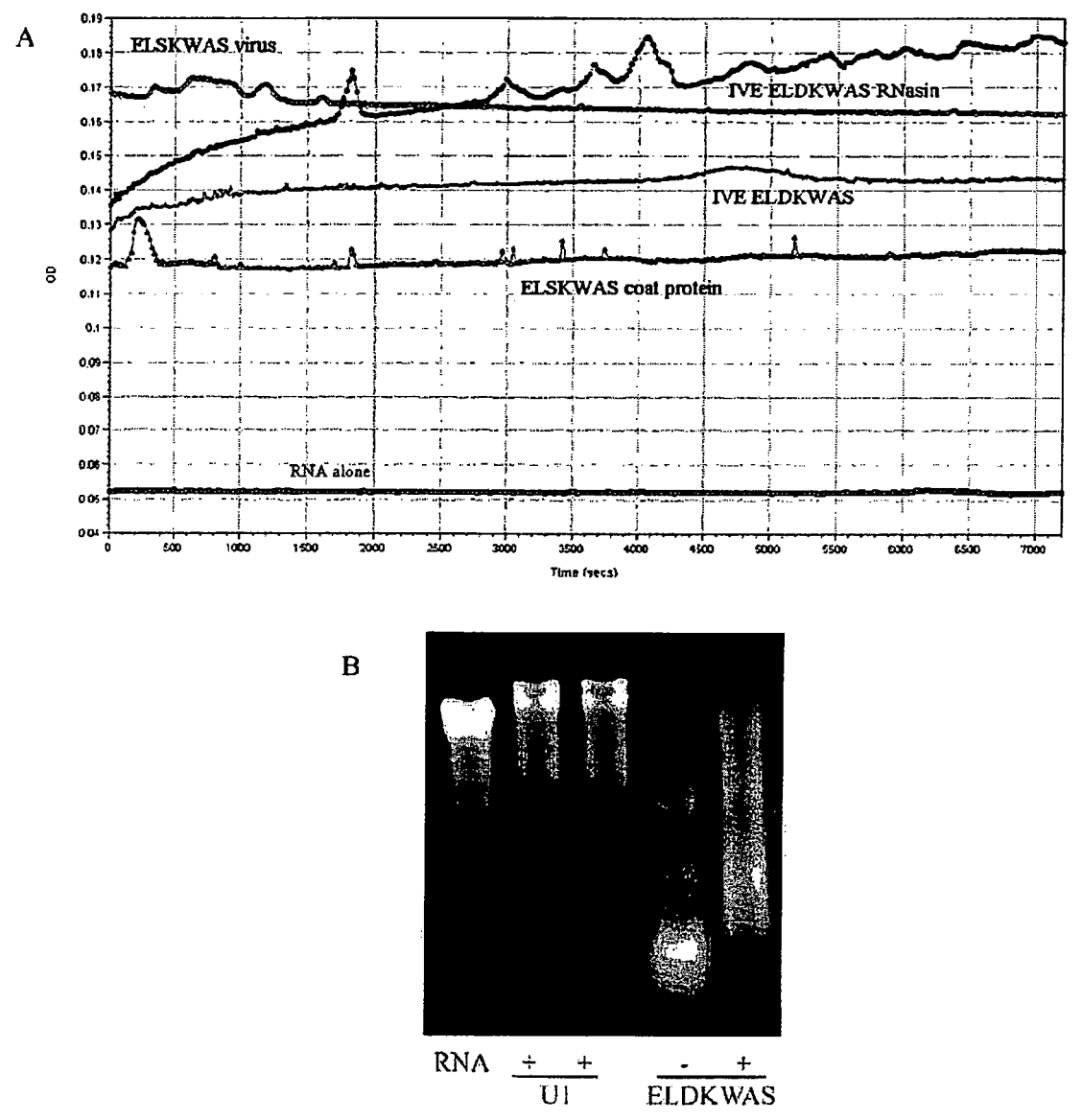

FIG. 18. (A) shows the A310 nm kinetic profile for reassembly reactions (IVE) with the ELDKWAS (Seq ID No:12) coat protein fusion, in the presence and absence of RNasin. The ELDKWAS (Seq ID No:12) virus control was present at the same molar concentration as the RNA in the reassembly reactions. (B) Agarose gel electrophoresis of reassembly reactions 5 hours after initiation. Reassembly reactions were performed in the presence (+) or absence (−) of RNasin and the coat protein employed is indicated. RNA alone, at the same concentration as in the reassembly reactions, was run as a control.

FIG. 19 shows images and data analysis for reassembly reactions viewed by transmission electron microscopy (TEM). The samples were negatively stained with 1% phosphotungstic acid, dried and stored at RT until visualized using a Philips CM120 TEM, at 37,000× magnification. (A) Coat protein control sample (no RNA present) (B) reassembly reaction with the same coat protein concentration as in (A) but with TMV RNA present at 50 μg/ml. Image is for reassembly reaction performed in the presence of RNasin. The scale bar represents 200 nm. (C) Comparison of the normalized particle size distribution for reassembly reactions with the ELDKWAS (Seq ID No:12) coat protein fusion, performed in the presence and absence of RNasin. n indicates the number of rods counted in the electron microscopy images.

FIG. 20(A) shows the A310 nm kinetic profile for separate reassembly reactions (IVE) with the ELDKWAS (Seq ID No:12), Myc and HPV ep2 coat protein fusions, all performed in the presence of RNasin. Wild type TMV RNA was employed as a scaffold. The ELDKWAS (Seq ID No:12) virus control was present at the same molar concentration as the RNA in the reassembly reactions. The RNA alone control is also shown, however, the coat protein alone and HPV ep2 and Myc virus controls are omitted for clarity. (B) shows the A310 nm kinetic profile for bivalent reassembly reactions (IVE) with the ELDKWAS (Seq ID No:12), Myc and HPV ep2 coat protein fusions taken in pair wise combinations. All reassembly reactions were performed in the presence of RNasin and wild type TMV RNA was employed as a scaffold. The ELDKWAS (Seq ID No:12) virus control was present at the same molar concentration as the RNA in the reassembly reactions. The RNA alone control is also shown, however, the coat protein alone and HPV ep2 and Myc virus controls are omitted for clarity.

FIG. 21 shows MALDI and SDS-PAGE data for the CRPV 2.1 coat protein fusion. (A) MALDI TOF trace showing the spectrum for purified CRPV 2.1 coat protein fusion. The predicted sequence weight for the protein, with the Met cleaved is 19320 Da, in excellent agreement with the observed molecular weight. (B) SDS-PAGE gel for the CRPV 2.1 coat protein fusion, showing a protein purity of greater than 97% for the final virus preparation.

Figure 22:
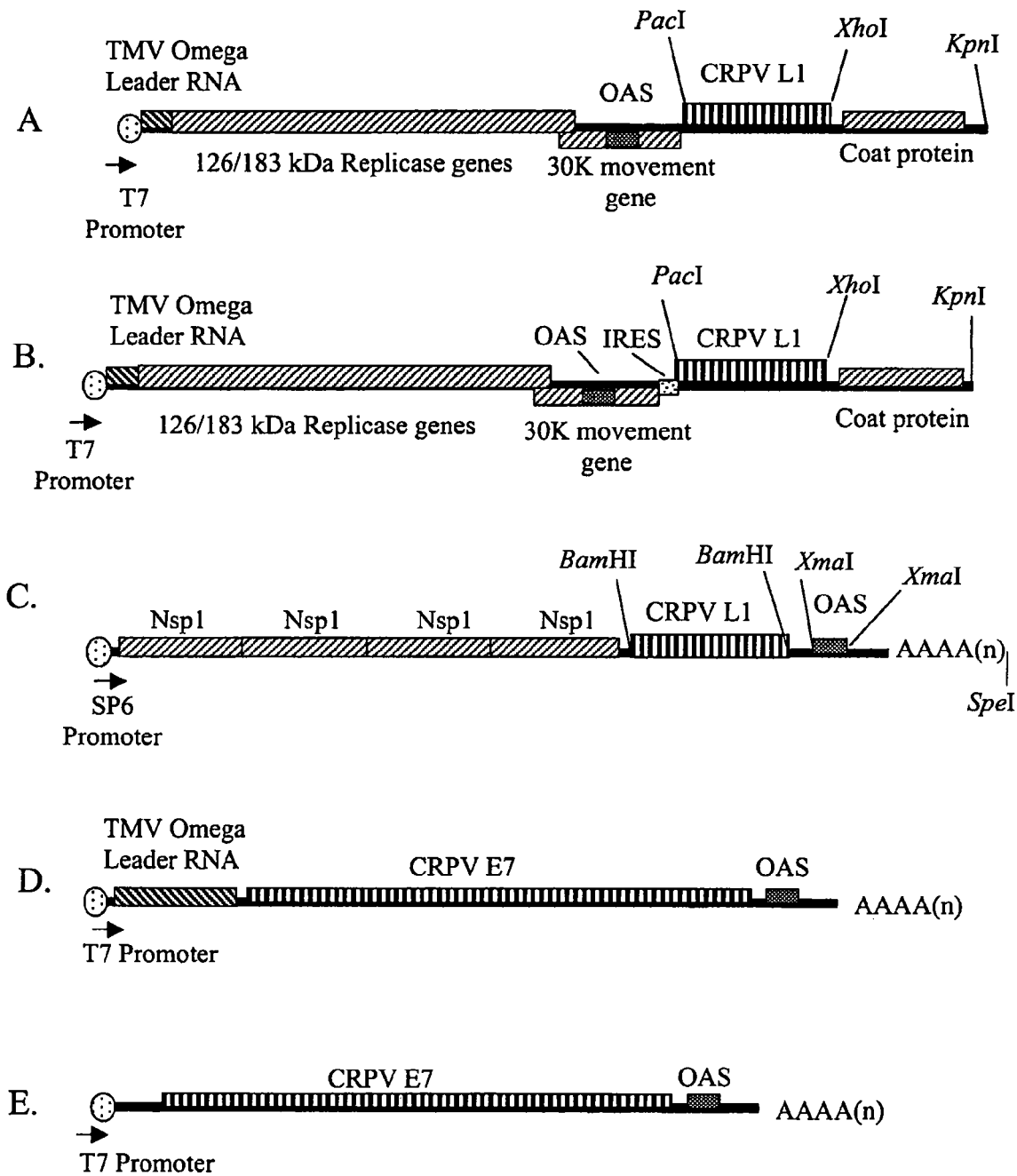

FIG. 22 shows various RNA constructs which may be used as a scaffold for the reassembly of multivalent TMV-based vaccines and which impart bifunctionality to the reconstituted virion, by virtue of the gene (s) that they encode. (A) TMV RNA containing a structural or non-structural gene. (B) TMV RNA containing IRES structural or non-structural gene. (C) Alphavirus replicon containing TMV OAS and structural or non-structural gene. (D) Chimeric mRNA containing TMV OAS and Omega with structural, non-structural or immune modulatory gene. (E) Chimeric mRNA containing TMV OAS with structural, non-structural or immune modulatory gene. For illustrative purposes the Figure shows the CRPV L1 or CRPV E7 genes in the RNA constructs. However, melanoma associated gene e.g. p15e, GP100 or any other structural or non-structural gene can replace these CRPV-associated genes.

FIG. 23 shows humoral responses to TMV coat fusion vaccines as measured by ELISA against the peptide. Sera were collected 10 days post vaccine 3 (pV3), serially diluted onto ELISA plates coated with either a c-myc-BSA conjugate or a foreign antigen (FNR) V5 fusion. Plates were then reacted with anti-mouse HRP and positives were visualized using a colorimetric substrate, and quantitated using statistical software. Commercially available positive controls were used as standards.

Figure 24:
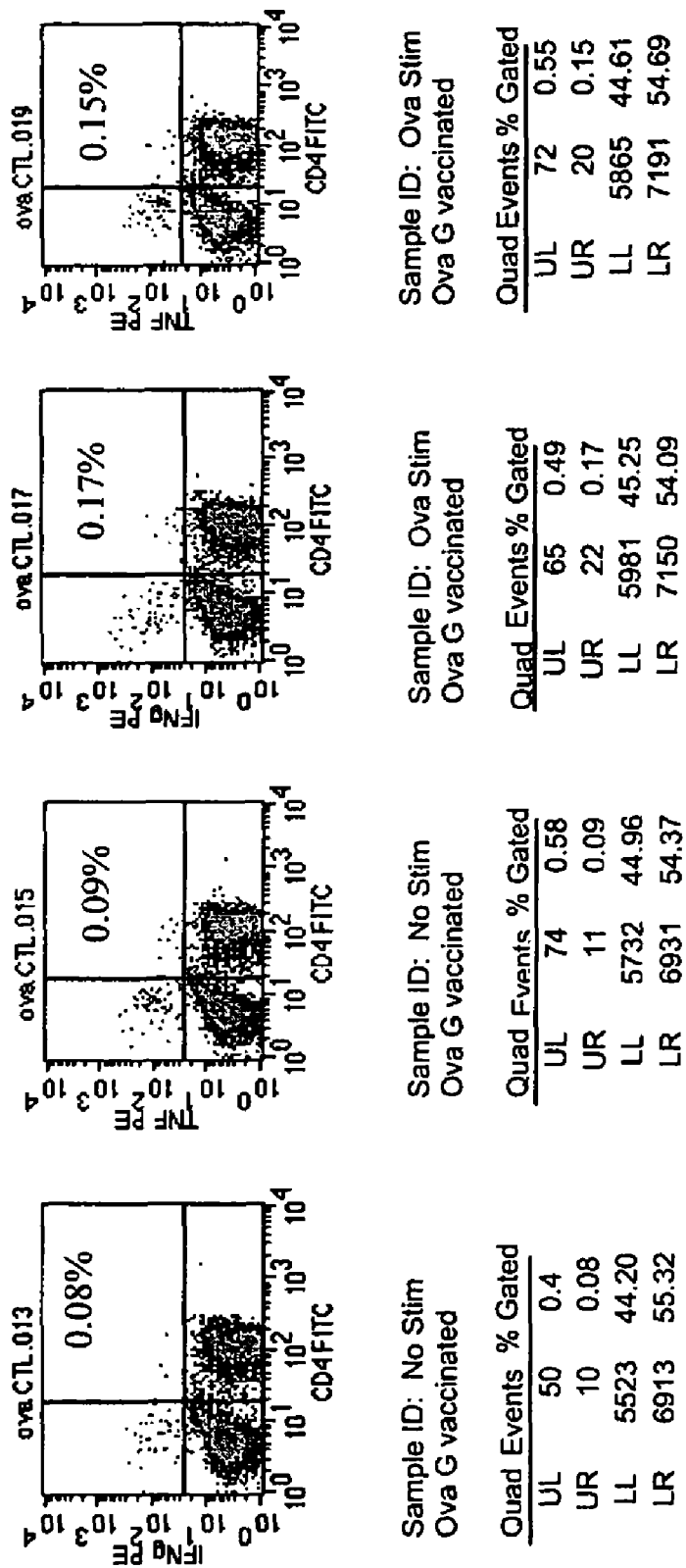

FIG. 24 shows the cellular response to TMV ova G vaccination as measured by fluorescent assisted cell sorting (FACS). Spleens from animals vaccinated with TMV ova G were harvested, and then cultured with 1 0g/ml ova peptide for 5 hours in the presence of Brefeldin A. Cells were then fixed, incubated with anti-CD4-FITC or anti-CD8-FITC antibodies, and then refixed and permeabilized. Cells were then incubated with anti-IFN-PE or anti-TNF-PE, and then visualized for PE and FITC staining by flow cytometry.

DETAILED DESCRIPTION OF THE INVENTION

Definitions and Abbreviations

In order to facilitate understanding of the invention, certain terms used throughout are herein defined:

"GM-CSF" means Granulocyte-Macrophage Colony Stimulating Factor. GM-CSF may increase the immunogenicity of antigens by stimulating antibody production mechanisms.

"Non-native" means not derived or obtained from the same species.

"Native" means derived or obtained from the same species.

"IgG" means immunoglobulin-G.

"Intergenic sequences" means the non-coding DNA sequences, wherein the viral origin of replication is situated, that are located between open reading frames of viruses.

"OAS" means origin of assembly sequence. The origin of assembly sequence is necessary for assembling the RNA molecule with viral coat proteins into a viral particle.

"Reconstituted protein" means the isolated and hydrated form of protein from a complex protein mixture "IL4" means interleukin 4, a cytokine that activates immune cells, especially B cells "IL1b" means Interleukin 1, beta subtype, a cytokine that activates immune cells "IL1b peptide" means a 9 amino acid section of IL1b that can stimulate T cells "IFNγ" means interferon, gamma subtype, a cytokine that activates immune cells, especially T cells "TMV" means tobacco mosaic virus "VLP" means virus like particle "Th1" means T-helper type one immune response, which is characterized by both antibody and cellular immunity "Th2" means T-helper type two immune response, which is characterized by primarily an antibody response "IVE" means in vitro encapsidation "RNA" means ribonucleic acid "DNA" means deoxyribonucleic acid "HA" means a peptide sequence derived from influenza hemaglutinin "V5" means a peptide sequence derived from simian virus 5

"myc or Myc" means the peptide derived from the myc oncogene

"N" position means the position the peptide or modification is inserted, at the N terminal location of coat protein "L" position means the position the peptide or modification is inserted, at the extracellular loop location of coat protein "G or GPAT" means the position the peptide or modification is inserted, at four amino acids from the C terminal location of coat protein "C" position means the position the peptide or modification is inserted, at the C terminal location of coat protein "Cys" means the amino acid Cysteine "20S" subunit describes the sedimentation profile of the 34 subunit coat protein disk in a density gradient "4S" subunit describes the sedimentation profile of the 4 subunit coat in a density gradient, which is an intermediate to the formation of a 20S disk "kDa" means kiloDalton, which refers to the molecular weight or mass of the protein "TEM" means transmission electron microscopy "RT" means room temperature "4 C" means 4 degrees Celsius, or near zero Fahrenheit "PAGE" means polyacrylamide agarose gel electrophoresis "SDS" means sodium dodecyl sulfate, a detergent "PEG" means poly ethylene glycol (molecular weight 6000-8000) "NaCl" means sodium chloride, or salt "DEAE" mean diethyl aminoethyl, a molecule used on anion exchange resins "PO4" means phosphate "pyro PO4" means pyrophosphate "SU" mean subunits "CRPV" means cottontail rabbit papillomavirus "ROPV" means rabbit oral papillomavirus "HPV" means human papillomavirus "OVA" means ovalbumin "GJ" means green juice, or total plant homogenate "S1" means clarified plant extract supernatant "S2" means supernatant derived from the S1 insoluble material by resuspension at pH 7

"BSA" means bovine serum albumin

"MW MALDI" means molecular weight mass determination by Matrix Assisted Laser Desorption Ionisation mass spectrometry "w/v" means weight per volume "OD" means optical density "DDT" means Dithiothreitol "RNAse" is an ubiquitous cellular enzyme that degrades RNA "RNAsin" is a commercially available RNase inhibitor "DEPC" is diethyl pyro carbonate, a chemical inhibitor of RNAse activity "Nab" means neutralizing antibody "L1" means papillomavirus capsid protein L1

"L2" means papillomavirus capsid protein L2

"E1, 2, 4, 6, 7, and E8" are papillomavirus early gene products

"CTL" means cytotoxic T lymphocyte

"SFV" means semliki forest virus

"IRES" means internal ribosomal entry site, which allows for the initiation of translation in the middle (or anywhere that is not at the first ATG) of the RNA "ORF" means open reading frame, the functional unit of RNA, which when translated encodes a protein "B16" means the mouse melanoma tumor cell line named B16

"SPDP" N-succinimidyl-3-(2-pyridyldithio)propionate

"BCA assay" Protein assay based on bicinchoninic acid

The present invention relates to a novel method for for the colorimetric detection and quantitation of total protein.

The present invention relates to a novel method for construction of a plurality of vaccines and pharmaceuticals using viruses, such as the tobacco mosaic virus (TMV). In broad terms, the invention is practiced in a manner depicted generically in FIGS. 1-6, as described below.

The description of the present invention is first provided in general terms, followed by a more detailed description that includes many biochemical procedures.

Figure 1:
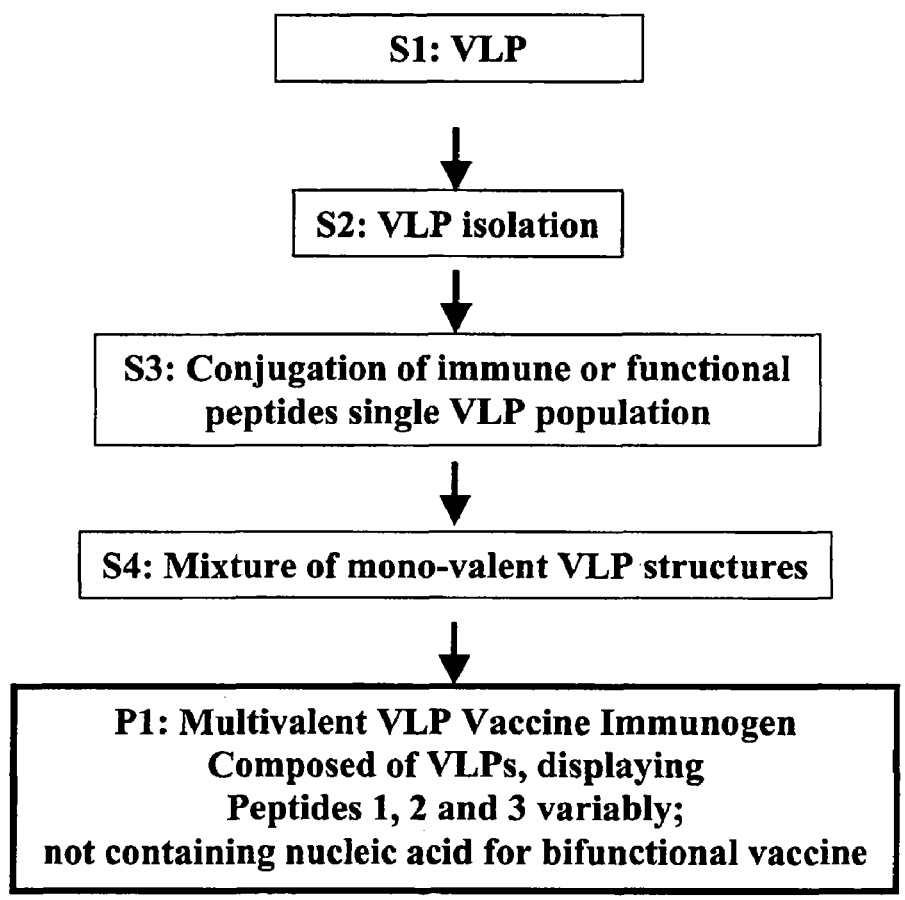

Standard methodologies can produce a pseudo-multivalent vaccine product by a chemical conjugation process outlined in FIG. 1. VLP particles are produced (S1) and isolated (S2). Individual peptides are individually chemically conjugated to the surface of independent lots of VLPs (S3) to produce distinct populations of VLPs, each displaying a unique peptide adduct. It is possible to conceive that multiple peptides could be simultaneously conjugated on the surface of the same population of VLPs to produce VLPs with a random distribution of unique peptides. The distinct populations of immune particles are then mixed (S4) to produce a population of VLP particles with distinct peptides covalently attached to the surface (P1). The resulting product will display distinct peptides in its mixture, but each will be independently taken up by immune cells and independently used to stimulate the immune system. There will be a lack of synergy between the fused peptides since there is no special connection between different peptides; each functions independently.

The described invention exploits the unique properties of the tobacco mosaic virus (TMV) that is amenable to the procedures outlined in FIG. 1, but also new methods (FIG. 2) with significant advantages. As represented by the box S5 in FIG. 1, a TMV virion is constructed with a surface associated amino acid allowing for improved chemical conjugation. This can be the presence of a unique, surface associated cysteine or lysine residue, although other methods can be employed. Large quantities of TMV are produced (S6) using, for instance, tobacco plants that are infected with the desired strain of TMV, then processed as described in co-pending patent application Ser. No. 09/962,527 filed Sep. 24, 2001, entitled PROCESS FOR ISOLATING AND PURIFYING VITAMINES AND SUGARS FROM PLANT SOURCES, and related U.S. Pat. Nos. 6,303,779, 6,033,895 and 6,037,456 all commonly assigned to Large Scale Biology Corporation, Vacaville, Calif., all of which are incorporated herein by reference in their entirety. Once large quantities of TMV are available, a process that is described in greater detail below disrupts the TMV in order to produce a large number of subunits (SU) or 20S disks, as represented by the box S7 and S8. The subunits are then separated at step S9 to form a plurality of subunits, each to be processed separately, as is described in greater detail below. As represented by step S9, each individual subunit group is subjected to a conjugation reaction in order to add predetermined components, such as a functional peptide, epitope, proteins or nucleic acid sequence to the subunits in that subunit group, in a manner that is described in greater detail below. As represented at step S10, pluralities of groups of subunits are now constructed into a single VLP structure where each subunit having specific epitopes, peptides, proteins or nucleotides attached thereto. TMV 20S disks naturally reassociate to form a rod-shaped virion surrounding an RNA molecule containing a unique sequence termed the TMV ori, or origin of assembly (OAS). This produces a multivalent vaccine (P2) that is not equivalent to a simple mixing reaction. Multifunctional peptide or nucleic acid adducts are linked physically to one another allowing each to synergistically enhance the cellular uptake of the VLP vaccine, immune processing, number of immune peptides presented to the immune system and the nature of the stimulated immune response. The simultaneous presentation of each peptide or nucleic acid component on the same VLP, rather than on distinct, unlinked VLP populations, is predicted to enhance the effectiveness of the VLP vaccine and lower the lower dose.

Further basic steps in the method of the present invention are depicted in FIG. 2. Specifically, at step S10 a specific recombinant RNA sequence is selected to be the scaffold for assembly of the TMV VLPs. The specific VLP subunits selected in step S10 are combined with the RNA selected to form a reassembled TMV via a process that is described in greater detail below. The RNA can act only as a structural scaffold and could represent only the TMV RNA itself, not offering any augmented function other than a building block of the new VLP vaccine. However, recombinant RNAs can be constructed containing the TMV ori (S10) that also encode proteins. Once the VLP is taken up in immune cells, the TMV virion has unique function. It is preferentially bound by ribosomes and disassembled by a co-translational mechanism (Mundry et al., J Gen Virol. April 1991; 72 (Pt 4):769-77). This would allow the efficient translation of this RNA so that the encoded protein is produced within the host immune cells. The encoded protein can either be an intact antigen to stimulate humoral or cellular immune responses against the targeted pathogen or cancer. Conversely, the RNA could encode immune stimulatory proteins (enhancing the amplitude of immune response) or modulatory proteins (insuring the direction, Th1 or Th2, of the immune response). This combination of protein elements that stimulate the immune response, as well as promoting the efficiency and effectiveness of the response, —in combination with an encoded nucleic acid component that is functional for augmenting the immune response, makes this vaccine truly bifunctional.

It should be noted that RNA is inherently unstable as a 'naked' element, or one not coated with a protective protein coating. However, it has an advantage over DNA in nucleic acid vaccines since it promotes translation of the desired product within immune cells, but is degraded and does not risk the immunized host with DNA recombination and the associated oncologic events. 'Naked' or uncoated nucleic acid vaccines of RNA or DNA types are very inefficient, where milligram (mg) quantities of DNA are required for any immune response in humans. Out of the mg of vaccine administered, picograms or less are taken up by immune cells. This results in expensive manufacturing and formulation costs, and very inefficient unpredictable immune responses. This invention allows the 'naked' RNA encoding important antigens or immune enhancing proteins to be coated and protected within the VLP structure of TMV. Such coating enhances the stability of the RNA and improves the delivery efficiency.

VLP vaccines are not dependent only on chemical conjugation to add immune peptides to their surface. The art describes methods for generating VLP vaccine through the genetic fusion of immunologically relevant peptides to the surface of VLPs. This process is described in FIG. 3. In this case, individual (S11) or multiple (S14) peptides are fused to the surface of the VLP protein through recombinant DNA procedures where the protein coding sequence for the immune peptide is fused to that of the VLP structure. Each individual or multi-peptide displayed VLP structure is purified (S11) and then qualified for its properties (S12). A multivalent vaccine is constructed by mixing either individual VLP populations displaying one or more peptides by genetic fusion (S13) or simply using a single population of VLP that is displaying more than one peptide by genetic means (S14). These procedures produce a multivalent VLP immunogen composed of multiple separate VLP populations, each displaying a unique immune peptide (P3). This approach suffers from the same limitations of the vaccines produced in FIG. 1 where little to no synergistic activity can be predicted by the simple mixture of non-linked peptides. Further, the VLP vaccines lack a nucleic acid component and are simply single functional vaccines—only providing a protein-based signal to the immune system.

This invention overcomes these difficulties by allowing truly multi-valent and multi-functional vaccines to be derived. TMV is amenable to the same procedures described in FIG. 3 to produce mixtures of VLPs each with unique genetic fusions. However, its unique properties permit the procedure described in FIG. 4. Individual TMV virions can be prepared with single or multiple peptides by genetic means (S15). Each individual virion is isolated (S15) and qualified. Each TMV virion is separately disassembled (S16) and SU are prepared (S17) composed of 20S disks displaying a unique array of immune peptides. This plurality of SU are then reassembled surrounding a RNA containing the TMV ori to produce TMV VLP (S18). The final product is indeed a VLP vaccine that displays multiple immune peptides simultaneously on the surface of each VLP (P4) and contains RNA that functions both as a scaffold for VLP assembly and as a separate immune stimulus. The advantages of this approach are the same as described above in that the particle is multi-functional in terms of the plurality of immune, immune modulatory, immune stimulatory or cell uptake facilitating peptides simultaneously displayed on the surface of the VLP. This allows more efficient cellular uptake, processing and immune stimulation resulting in reduced dose and improved immune protection. The RNA again contributes essential functions beyond a scaffolding device. It can encode intact antigens, immune modulatory, immune stimulatory proteins to further augment the immune response. The RNA is protected within the VLP and is delivered efficiently to the cellular translation apparatus by the natural functions of TMV VLPs.

Figure 3:
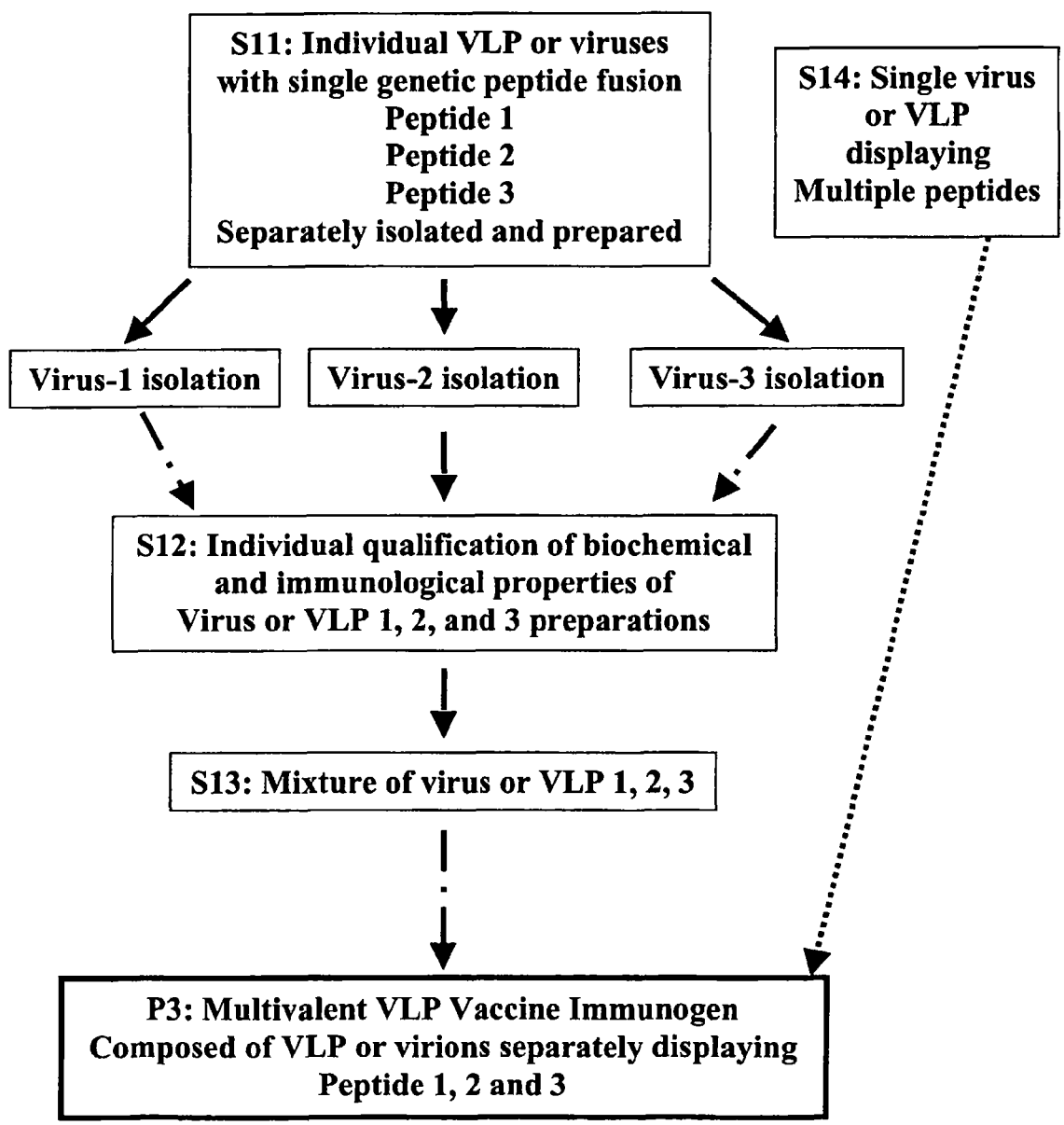

It should be understood that the above description is only a basic framework of steps upon which the present invention functions, and a basic understanding of the platform for constructing vaccines and pharmaceutical products in accordance with the present invention. The steps outlined in the flow diagrams in FIG. 2 and FIG. 4 are illustrated visually in FIGS. 5 and 6. Two further points should be noted with regard to the basic frameworks outlined in FIGS. 1 to 4. Firstly these figures indicate that various vaccine compositions contain 3 unique epitopes either displayed on separate VLPs or virions or all reassembled onto one VLP or virion. The number three was chosen purely for illustrative purposes and it should be understood that any number of epitopes can be recombined to form a multivalent vaccine. Secondly the entity displayed on the surface of the VLP or virion need not be limited to a peptide epitope as indicated in FIGS. 3 and 4. The displayed entity can also be a nucleotide, introduced by chemical fusion, or a complete protein, introduced by either chemical or genetic fusion. Furthermore all possible combinations of nucleotide, peptide epitope and complete protein, in terms of both number and ratio, can be envisioned for multivalent vaccine reassembly. For example peptide 1, nucleotide A and complete protein X, each displayed on separate virions or VLPs can be combined to yield a multivalent VLP vaccine similar to P3 in FIG. 3. Alternatively separate pools of 20S disks each displaying peptide 1, nucleotide A and complete protein X can be reassembled in vitro to generate a multivalent vaccine similar to P4 in FIG. 4, where all entities reside on a single VLP or virion.

Following are a series of detailed examples, which illustrate the general flow diagrams described on the preceding pages.

Example 1

Peptide Fusions and Solubility as a Function of pH

The current industry standard for success with peptide fusions is 40-50%. To improve on this a series of fusions were tested at multiple insertion locations on the TMV U1 coat protein and each fusion was extracted under multiple conditions, to determine the influence of fusion position on virus solubility. This example describes the influence of genetic fusion position on the isolation of recombinant TMV viruses (step S15, FIG. 4).

Figure 7:
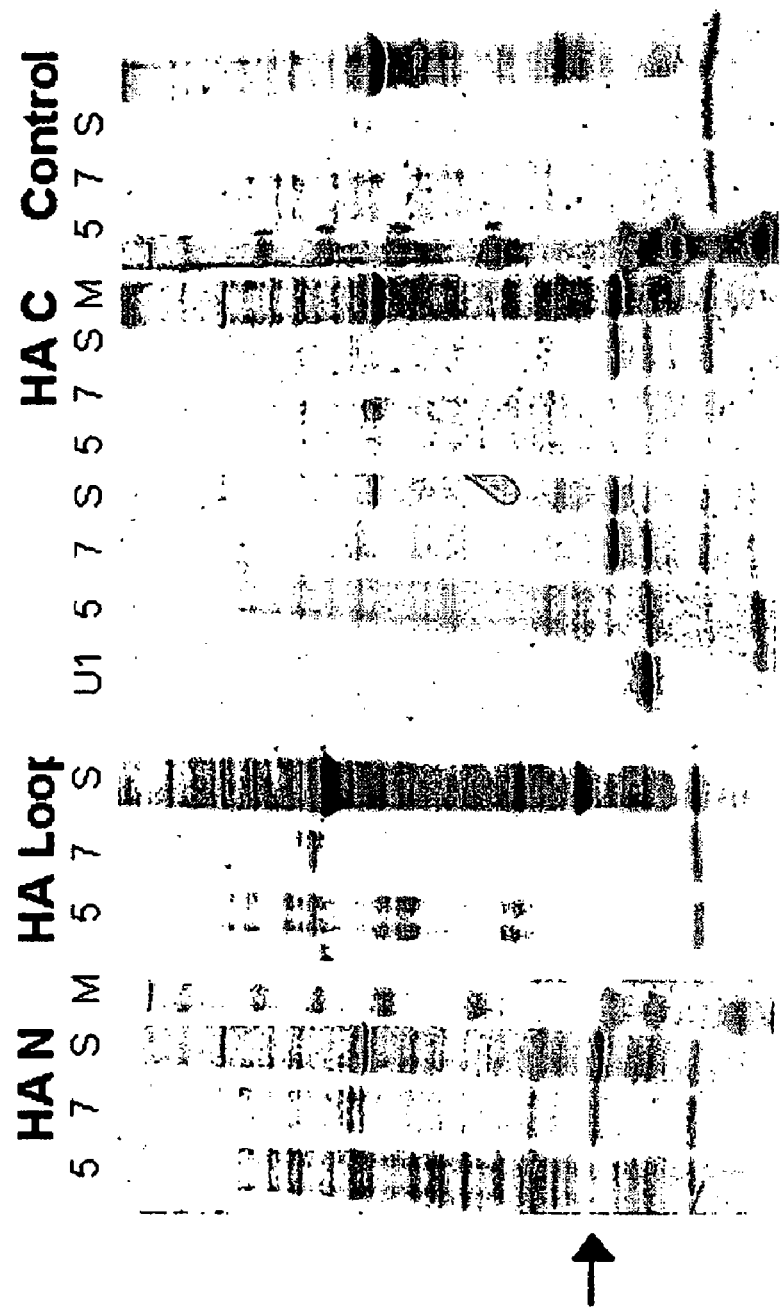

FIG. 7 illustrates results for the fusion HA, inserted at four different locations on the U1 coat protein; the N terminal, C terminal, surface loop (L) and 4 amino acids from the C terminus (GPAT). Clear differences in the extent of cleavage and virus solubility were evident. Approximately 100% HA GPAT was cleaved back to wild type U1 protein molecular weight when extracted at pH 5. Re-extraction at pH 7 improved full-length yield to 50%. Tissue extraction in SDS PAGE buffer yielded full-length coat fusion product, suggesting that cleavage was occurring during processing. This also occurred at the C terminal fusion location, although to a lesser extent. The processing of coat fusions appears to be site specific, as locating the epitope at the N-terminus yielded a full-length product. No virus was recovered at pH 5 or pH 7 with the HA epitope at the loop position; the SDS-PAGE buffer grind indicated that loop insertion was expressed but resulted in an insoluble product. For fusions that show cleavage during extraction e.g. HA GPAT, protease inhibitor cocktails can be incorporated to reduce or eliminate cleavage. Alternatively, other strains of *N. tobaccum* can be screened to identify hosts with reduced protease activity.

Table 1 summarizes the influence of epitope location on the solubility and relative recoveries for HA and two additional model epitope fusions, V5 and Myc. The V5, HA and myc epitope TMV fusion proteins were tested for reactivity to peptide specific antibodies by Western analysis, to confirm the identity and integrity of each fusion peptide (data not shown).

TABLE 1

Expression levels by insertion site for three antibody binding epitopes.

| | Position of insert and Extraction buffer pH | | | | | | | |
|---|---|---|---|---|---|---|---|---|
| | N | | L | | GPAT | | C | |
| Fusion name | pH 5 | pH 7 | pH 5 | pH 7 | pH 5 | pH 7 | pH 5 | pH 7 |
| V5 | +++ | ++ | + | + | ++ | + | ++ | + |
| HA | − | ++ | − | − | − | ++ | − | ++ |
| Myc | +++ | ++ | − | +/− | ++ | +++ | ++ | ++ |

Following the confirmation of expression with the three model fusions the list of fusions was expanded to include clinically relevant epitopes of papillomavirus and melanoma as well as immuostimulatory and cell fusion epitopes aimed at incorporating biological functionality to reassembled fusion products. Table 2 summarizes the solubility results for all the epitope fusions. Of the 18 target epitopes attempted 15 were successfully expressed as soluble products, an 83% success rate. This represented a doubling of the previous industry standard of 40% expression/solubility. This improvement is due to the rotation of the insert position, performed in parallel with the extraction with two different pH buffers.

TABLE 2

15 of 18 peptides have been expressed in frame with TMV U1 coat at either the N-terminus (N) the GPAT position (G) or at the C terminal location (C). Those fusions that were soluble in either pH 5 or 7 extraction buffer from leaf punch grinds (~200 μg leaf tissue) are indicated in the Solubility column. Those fusions that were also successfully scaled up (>500 grams leaf tissue) are also indicated.

| Peptides | Name | Solubility | Scalability |
|---|---|---|---|
| GKPIPNPLLGLDSTK (Seq ID No: 1) | V5 | N, G, C | N, G, C |
| YPYDVPDYAK (Seq ID No: 2) | HA | N, G, C | G, C |
| EQKLISEEDLK (Seq ID No: 3) | c-myc | N, G, C | N, G, C |
| *Papillomavirus* | | | |
| VGPLDIVPEVADPGGPTLV (Seq ID No: 4) | CRPV 2.1 | N, G | G |
| PGGPTLVSLHELPAETPY (Seq ID No: 5) | CRPV 2.2 | N, G | G |
| VGPLEVIPEAVDPAGSSIV (Seq ID No: 6) | ROPV 2.1 | N, G | G |
| PAGSSIVPLEEYPAEIPT (Seq ID No: 7) | ROPV 2.2 | N, G | G |
| AALQAIELM (Seq ID No: 8) | HPV16 ep2 | N | N |
| *Melanoma* | | | |
| SVYDFFVWL (Seq ID No: 9) | TRP-2181-188 | — | |
| KSPWFTTL (Seq ID No: 10) | p15E 604-611 | — | |
| SIINFEKL (Seq ID No: 11) | OVA | N, G, C | N, G |
| *HIV* | | | |
| ELDKWAS (Seq ID No: 12) | ELDKWAS | N | N |
| *Immunostimulatory* | | | |
| CEYNVFHNKTFELPRA (Seq ID No: 13) | Th SH 45-60 | G, C | |
| QYIKANSKFIGITELKK (Seq ID No: 14) | P2 TT 830-846 | — | |
| VQGEESNDK (Seq ID No: 15) | IL1β | N, G, C | N |
| *Cell fusion* | | | |
| FAGVVLAGAALGVATAAQI (Seq ID No: 16) | F1 Measles | L, G | |
| SGRGDSG (Seq ID No: 17) | integrin | N, G, C | N |
| GYIGSR (Seq ID No: 18) | laminin | N, G, C | N |

Example 2

Improving Solubility and Accumulation by Modifying the Linker Amino Acids

Figure 8:
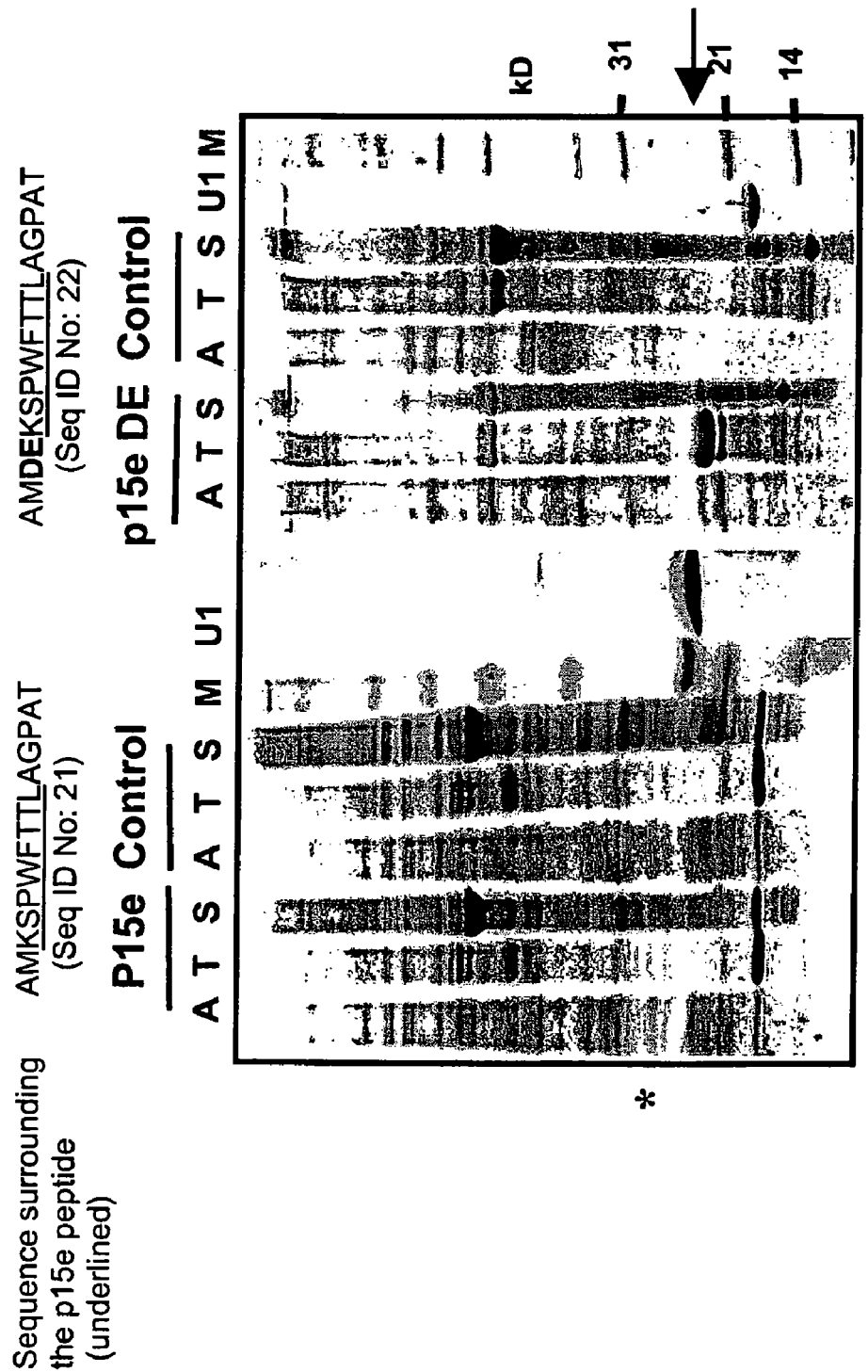

Molecular fusion of epitopes to TMV sometimes fail to accumulate when aromatic (for example W) or hydrophobic amino acids are present in the peptide. For example, p15e, a mouse melanoma antigen, contains the aromatic amino acid tryptophan (W). This peptide, when introduced onto the N or C-terminal positions on U1 coat, caused virus instability and no TMV systemic infection was observed. Applicant reasoned that to create a more favorable environment for peptide solubility, flanking amino acids could be added to increase hydrophilic interactions, counteracting the negative effects on virus assembly or stability when amino acids like W are introduced onto the solvent exposed surface of coat protein. Aspartic Acid (D) and Glutamic Acid (E) are amino acids that are charged, and were used to show that such a method will rescue the insoluble fusion of p15e to TMV coat (FIG. 8). Before addition of DE adjacent to the p15e peptide, no accumulation of product was observed (*). After addition DE to p15e, product accumulation is clearly visible (arrow). Other amino acids could also be used to alleviate negative effects of peptide composition on TMV accumulation, such as Asparagine (N), Glutamine (Q), Histidine (H), Lysine (K), Serine (S) or Threonine (T). The number and type of flanking amino acids that are sufficient to overcome negative effects on TMV expression levels or assembly may be fusion-peptide specific, and may need to be tested empirically for each peptide. This example illustrates the use of mitigating sequences to permit isolation of genetic fusions (S15, FIG. 4)

Example 3

Chemically Conjugated Epitope Fusions to TMV U1

Only a percentage (70-80%; see Example 1) of genetic fusions are capable of functional VLP formation for many plant viruses. Many fusions fail to accumulate while others are simply insoluble. The present invention includes construction of coat protein fusions containing cysteine (Cys) residues as either N-terminal or surface loop fusions. The initial fusions to TMV U1, and to other tobamovirus coat proteins showing good expression in the U1 vector, are composed of glycine-cysteine-glycine (GCG) or GGCGG (Seq ID No: 23) as N- and surface loop fusions (FIG. 9A (1)). Previous LSBC experiences have indicated that cysteine residues are tolerated on the virion surface and that under the reducing conditions of the plant cytosol, no disulfide bridges are formed between coat protein subunits or host proteins. The production of coat protein with surface exposed Cys residues allows peptide conjugation to the TMV virions through conjugation using heterobifunctional chemical cross-linking reagents, e.g. N-succinimidyl-3-(2-pyridyldithio) propionate (SPDP). SPDP allows coupling of free sulfhydryl group with a free amine group, such as that found on lysine (K), at neutral pH under mild reaction conditions. SPDP fused immuno-conjugates have been used extensively in in vivo administrations. Peptides used for initial studies and comparative biochemical response of the various tobamovirus coat proteins (CPs) are the c-myc tag (EQKLISEEDLK, Seq ID No: 3), the HA tag (YPYDVPDYAK, Seq ID No: 2) and the V5 tag (GKPIPNPLLGLDSTK, Seq ID No: 1). Each is synthesized (Sigma chemical) to contain a C-terminal lysine for conjugation to the sulfhydryl group. In addition to peptides, SPDP could be used to fuse the immune stimulatory single stranded DNA CpG polynucleotide using a thiolated 3' terminus to the TMV virions as well. An alternative approach is to introduce a different reactive amino acid, such as lysine, into the region of solvent exposed residues of TMV coat protein (FIG. 9A (2)), and synthesize peptides with a C terminal or N terminal cysteine for conjugation.

Figure 9B:
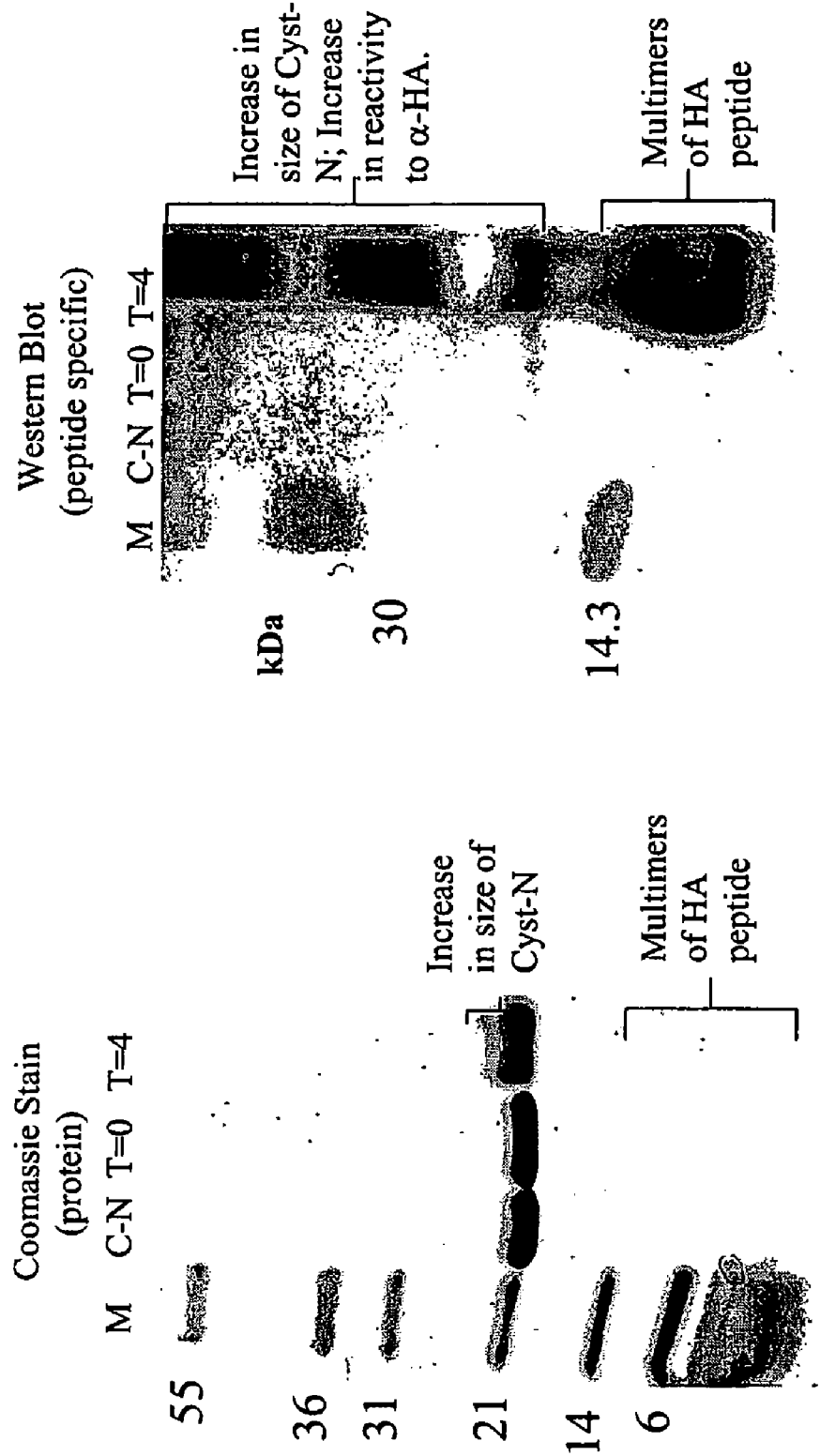

Initially, SPDP conjugations are tested for reactivity to cysteine containing TMV that is not disassembled. Cross-linking reactions are carried out using short chain, long chain and sulfo-NHS forms of SPDP as described (Hermanson, G. *Bioconjugate Techniques* 1996 Rockford Ill., Academic Press, and references therein). Peptide-SPDP adducts are mixed with cysteine TMV U1 virus and then analyzed 16 hours later for a size shift that represents physical association of the peptide with the virus. The procedure is then extended to 20S disks. An alternative approach was to use a less specific chemical conjugation strategy employing glutaraldehyde. The HA peptide was mixed with either TMV or N terminal cysteine TMV in the presence of glutaraldehyde. After a four hour incubation with glutaraldehyde, a HA peptide-TMV cysteine conjugate was formed and was visible as an increase in mass by Coomassie, as well as by an increase in apparent molecular weight by Western analysis (FIG. 9B). No such conjugate was present if wild type TMV (with no solvent exposed cysteine) was used in the conjugation reaction (data not shown). Conjugation by non-specific cross-linking agents, such as glutaraldehyde, leads to higher molecular weight aggregates as is clearly visible in the Western blot. Other conjugation reagents with more specific chemistry, such as SPDP, EDC or other heterobifunctional linkers, generate one to one or directional coat to fusion peptide chemistry, and result in more controlled conjugation reactions.

An alternative strategy is to assemble N cysteine coat into 20S discs, reassemble these discs with other discs that carry functional epitopes (ie, by molecular fusion) onto an RNA, and incubate the fully reassembled mixture with SPDP-associated peptide or moiety in order to add a new functionality. This is especially useful if the SPDP conjugation renders 20S discs chemically inert and unable to reassemble with other discs, or if the peptide that is carried interferes sterically with reassembly. As well, the ability to add a variety of agents after reassembling a monomer or a multimer has great utility. For example, SPDP conjugation of ssDNA such as CpG oligonucleotides may allow for the augmentation of immune modulation, which is greater than simply mixing the CpG with the vaccine. This could lead to better efficacy and or the potential to reduce the dose. This example illustrates the steps S3 (FIG. 1) and S9 (FIG. 2) as well as providing alternative routes to combine chemically and genetically attached epitopes.

Example 4

Electron Microscopy of TMV Coat Protein Fusions

Figure 10:
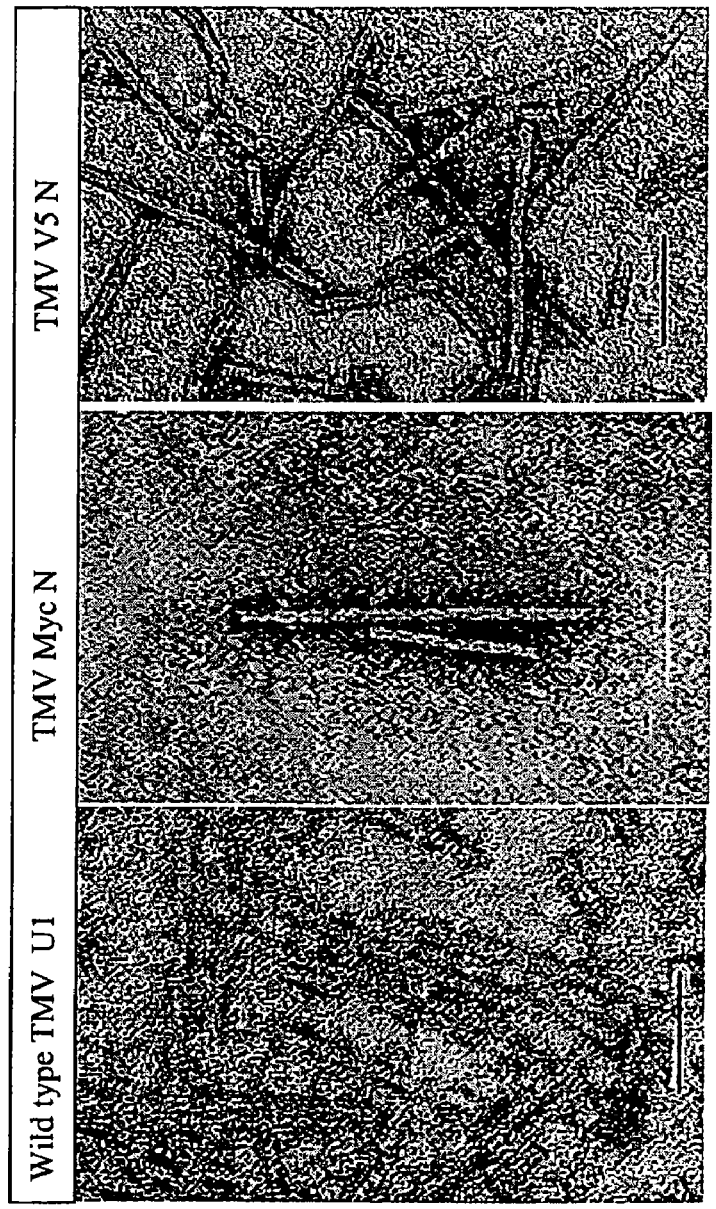

To determine the influence of the fusions on virus structure, transmission electron microscopy (TEM) was performed (FIG. 10). Wild type TMV rods have the dimensions 18-20 nm×300 nm. The N terminal epitope fusions of the model peptides V5 and Myc were visually similar the wild type U1 virus, as were the rod dimensions. This indicates that the fusion does not hinder normal coat protein reassembly in vivo and that the fusions constitute good candidates for in vitro reassembly.

Example 5

Extraction and Partitioning of Wild Type TMV U1

Figure 11A:
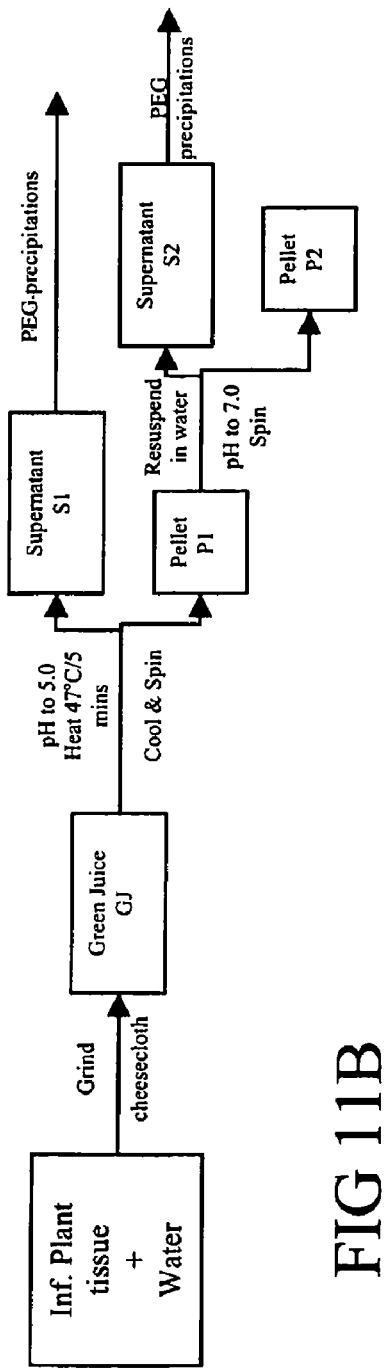

The extraction and processing of TMV U1 has been extensively discussed in the above mention commonly assigned U.S. Pat. Nos. 6,303,779, 6,033,895 and 6,037,456, which are incorporated herein by reference in their entirety. The processing is summarized in FIG. 11A. Briefly, a weighed mass of infected tissue is combined with two volumes of chilled water, containing 0.04% w/v sodium metabisulfite and grinding is preformed in a Waring blender. The homogenate is passed through 4 layers of cheesecloth to remove the fiber, leaving the green juice (GJ). The pH of the GJ is adjusted to 5.0. followed to heating to 47° C. for 5 minutes. After chilling the GJ is spun to precipitate insolubles, yielding a first supernatant. In cases where the virus partitions into the remaining pellet P1, the pellet is resuspended in water and adjusted to pH 7.0. Following a centrifuge spin the virus is recovered in a second supernatant and the final pellet P2 is discarded. To purify and concentrate the virus, two serial selective precipitations are performed on the first and second supernatants processing streams. Precipitation of the virus is achieved by adjusting the supernatants to 4% w/v polyethyleneglycol (PEG) and 4% w/v NaCl, and chilling for 30-60 minutes. Following a centrifuge spin the virus is recovered as a pellet and contaminating proteins remain in the supernatant, which is discarded.

Figure 11B:
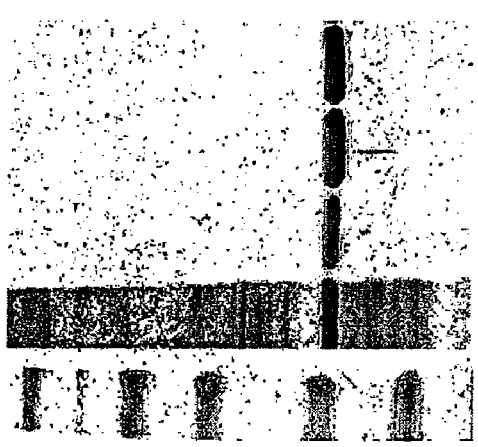

FIG. 11B and Table 3 show representative results for wild type TMV U1 isolated from *N. tabacum* MD609. The SDS gel clearly demonstrates that the process yields a final virus preparation of high purity. Using BSA as a standard the coat protein bands were quantified densitometrically and a material balance for the process performed to determine recovery (Table 3). From the data it is clear that the majority of the virus partitioned into the S1 process stream and with minimal losses during the PEG precipitation a total process recovery of 76% was achieved.

TABLE 3

Material balance for the isolation of TMV U1 from infected *N tabacum* MD609 plants. Data was generated from the densitometric analysis of the gel in FIG. 11, using a BSA standard curve.

| mg virus/ g FW | % in S1 | % in S2/P1 | Losses during S1 PEG1 | Losses during S1 PEG2 | Mg virus recovered/ g FW | Total process recovery |
|---|---|---|---|---|---|---|
| 1.7 | 86% | 14% | 9% | 2% | 1.3 | 76% |

Example 6

Influence of Epitope Fusion on Virus Extraction and Partitioning

The process outlined in Example 5 was employed for a selection of the coat protein fusions listed in Table 2. Material balances were performed to determine the partitioning of the virus between the S1 and S2 process streams, in addition to the total process recovery. The identity of each fusion was confirmed by MW MALDI. The results for these purifications are summarized in Table 4. From the table it is clear that the processing characteristics are epitope fusion and location dependent. A material balance on the extraction gave initial recoveries (S1+S2 process streams) from 90-100% (e.g. HPV ep2 N) to lower than 10% (e.g. V5 N). Partitioning between the S1 and S2 streams also varied substantially. Overall recoveries also ranged from 0.5% to 79%. Based on this data the cysteine N, Myc N and V5N coat protein fusions were carried forward to optimization studies to determine conditions which would improve overall process recoveries. This optimization is detailed in Examples 7 and 8 and illustrates process modifications that can be employed in order to isolate TMV virus displaying genetic fusions (step S15, FIG. 4)

TABLE 4

Virus partitioning and overall process recovery for various coat protein fusion epitopes.

| Fusion | % in S1 | % in S2 | Streams processed | Overall process recovery |
|---|---|---|---|---|
| Cysteine N | 10% | 44% | S2 | 0.5% |
| Myc #1 N | 38% | 26% | S1 and S2 | 13% |
| Myc #2 N | ~20% | 24% | S1 and S2 | 6% |
| Myc C | N/A | N/A | S1 and S2 | 13% |
| V5 #1 N | N/A | N/A | S1 | 2% |
| V5 #2 N | ~5% | ~5% | S1 and S2 | 3% |
| HPV ep2 N | 60% | 40% | S1 | 51% |
| OVA N | 26% | 50% | S1 and S2 | 79% |

Fusion location designation; N, N terminus; C, C terminus; GPAT, N terminal to GPAT sequence.
# indicates the purification run number for fusions isolated more than once.

Example 7

Influence of Sodium Chloride on Virus Extraction and Partitioning

The incorporation of sodium chloride into the extraction buffer was tested as a means to improve virus recovery and alter virus partitioning. GENEWARE-infected *N benthamiana* plants were harvested and the biomass split, to perform a head to head comparison of extraction in the presence and absence of salt. One half of the plant material was extracted in chilled water containing 0.04% sodium metabisulfite and the remaining biomass was extracted in a 50 mM-acetate buffer, pH 5.0, containing 4% w/v NaCl and 0.04% sodium metabisulfite. Processing was performed following the procedure outlined in Example 5. A comparison of the S1 and S2 fractions by SDS-PAGE, for the Cysteine N TMV fusions (FIG. 12), clearly illustrates that the presence of salt forces the virus to partition to the S1 fraction. This is favorable as the virus obtained from this stream is typically less contaminated by plant pigments and impurities. Also, from FIG. 11A it is clear that S1 partitioning is preferential to S2 partitioning as it reduces the number of processing steps.

A material balance for extractions in the presence and absence of salt is given in Table 5. From the data for Cysteine N, it is clear that the overall process recovery was improved substantially with the addition of salt; although the total virus extracted in both cases was identical, the virus loss in the absence of salt was 44% (remained associated with the P2 pellet) compared to only 7% with 4% w/v sodium chloride. Table 5 also has data for recovery and virus partitioning of the Myc N and V5N coat protein fusions during extraction. The benefits of sodium chloride are again evident, indicating that this process modification has general applicability.

TABLE 5

Material balance for the isolation of viruses displaying multiple epitopes from infected *N benthamiana* plants. Data was generated from the densitometric analysis of the SDS gels, using a BSA standard curve.

| Fusion | Buffer | mg virus/g FW | % in S1 | % in S2 | Losses during extraction |
|---|---|---|---|---|---|
| Cysteine N | No NaCl | 1.9 | 10% | 46% | 44% |
|  | 4% w/v NaCl | 1.9 | 88% | 6% | 7% |
| Myc N | No NaCl | 3.3 | 38% | 26% | 36% |
|  | 4% w/v NaCl | 2.9 | 90% | 8% | 2% |
| V5 N | No NaCl | 1.2 | ~5% | ~5% | 90% |
|  | 4% w/v NaCl | 1.2 | 63% | 0% | 37% |

Example 8

Influence of Salt and PEG Concentration of Virus Precipitation

Figure 13:
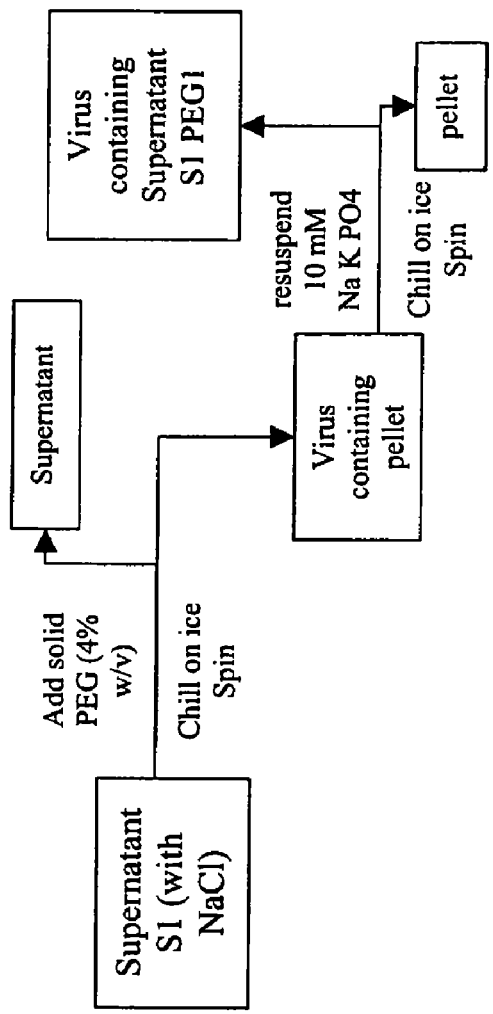
FIG. 13 shows a flow diagram for the precipitation of TMV virus in the presence of polyethylene glycol (PEG) and sodium chloride (NaCl).

As illustrated in FIG. 11 the virus in either the S1 or S2 processing streams is further purified and concentrated by a series of two PEG precipitations. The steps involved in the first PEG precipitation are outlined in the flow diagram below (FIG. 13). The S1 (or S2) supernatant is adjusted to 4% w/v polyethylene glycol and 4% W/C NaCl. If the supernatant already contains NaCl only solid PEG is added, dissolved with agitation and the sample chilled on ice. The precipitated virus is pelleted by centrifugation and the supernatant discarded. The virus-containing pellet is then resuspended in a low ionic strength buffer and a low speed clarification spin performed. This will pellet any residual pigment and aggregated contaminating plant proteins, leaving the virus in solution. This solution is then resubmitted to a second PEG precipitation by adjusting to 4% w/v PEG and 4% w/v NaCl and repeating the process.

Table 6 compares the recoveries obtained from the two-step PEG precipitation for wild-type TMV U1 and two coat protein fusions, Myc N and V5N. The standard procedure outlined in FIG. 13 resulted in poor recoveries for both coat protein fusions compared to the wild type U1. From the flow diagram the losses can result from incomplete precipitation of the virus by the PEG, or pelleting of the virus during the clarification step. A material balance around each step in the PEG precipitation indicated that for Myc N 4% w/v PEG was insufficient to pellet the virus and the majority remained in the supernatant. In this case an increase in the PEG concentration, to 8% w/v, was required and this modification improved recovery from 6% to 60%. For the VSN virus complete precipitation was achieved with 4% w/v PEG, however, the virus failed to remain in solution during the clarification spin. By resuspending the virus-containing pellet in 10 mM Na K PO4 containing 4% w/v NaCl, the virus remained soluble and recovery was increased from <1% to 95%. These two examples illustrate how the fusion can influence the virus properties and provide methods to maintain virus solubility during processing.

TABLE 6

Optimization of PEG precipitation steps for TMV coat protein fusions

| Fusion | Stream processed | Conditions | Losses during S1 PEG1 | Losses during S1 PEG2 | Recovery PEG precipitation steps |
|---|---|---|---|---|---|
| Wild type U1 | S1 | Standard | 9% | 2% | 89% |
| Myc N | S1 | Standard | 80% | 63% | 6% |
| V5N | S1 | Standard | ~95% | ~95% | <1% |
| Myc N | 1 | 8% w/v PEG Resuspend in 4% w/v NaCl | 25% | 20% | 60% |
| V5 N | 1 | Resuspend in 4% w/v NaCl | 5% | 1% | 94% |

Example 9

Generation of Free Coat Protein and 20S Disks

Figure 14:
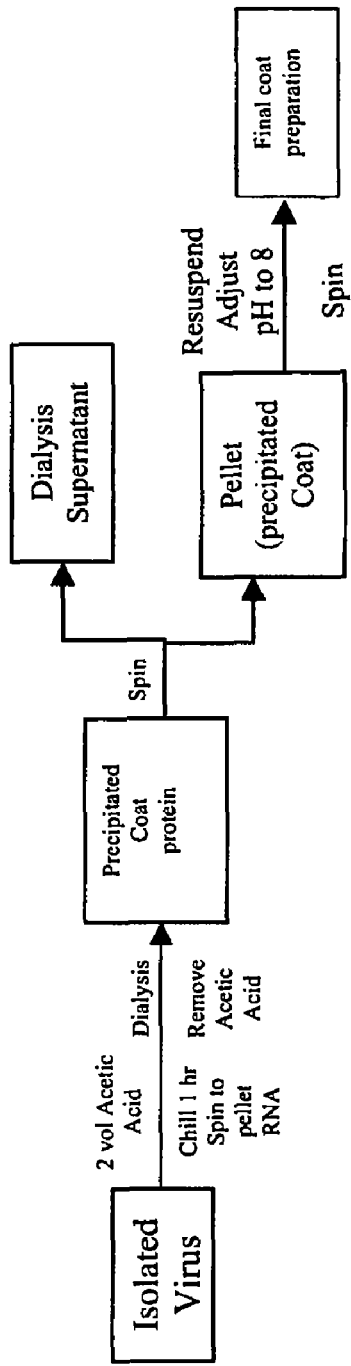
FIG. 14 shows a flow diagram for the generation of free coat protein from TMV virus.

This example illustrates in greater detail steps S7 and S8 (FIG. 2) and steps S16 and S17 (FIG. 4). Coat protein was generated from purified virus using a modified version of the protocol developed by Fraenkel Conrat (Virology 1957, 4, 1-4), which is summarized in FIG. 14. Briefly the virus was combined with 2 volumes of glacial acetic acid and incubated for 1 hour at 4° C., resulting in disassociation of the virus and degradation/precipitation of the RNA. Following centrifugation to remove the degraded RNA, the acetic acid was removed by dialysis. Alternatively an ultrafiltration/diafiltration can be employed to remove the majority of the acetic acid, prior to dialysis. With dialysis the coat protein precipitates at its isoelectric point. The precipitated coat protein was isolated by centrifugation and resuspended in water. By adjusting the pH to 8, the coat protein was resolubilized and subjected to a final spin to remove any remaining aggregated species.

This process was employed to generate a number of free coat protein fusions from purified virus. Table 7 summarizes the process recoveries for a selection of the epitope fusions for which coat protein was generated.

TABLE 7

Free coat protein generation for a selection of epitope fusions.

| Fusion | Acetic Acid removal | | Overall process recovery |
|---|---|---|---|
| | UF/DF | Dialysis | |
| HPV ep2 N | | + | 49% |
| ELDKWAS (Seq ID No: 12) N | | + | 68% |
| Myc C | + | | 50% |
| Myc N | + | | 38% |
| V5 N | + | | 34% |

Fusion location designation; N, N terminus; C, C terminus.

The quality of the coat protein was assessed by its ultraviolet absorption spectrum (Durham, J Mol Biol, 1972, 67: 289). The spectrum should have an absorbance maximum at 282 nm, an absorbance minimum at 251 nm and a maximum to minimum ratio between 2.0 and 2.5. A lower ratio indicates residual RNA contamination of the coat protein preparation. FIG. 15A shows the typical absorption spectrum for wild type TMV U1 coat protein. Table 8 summarizes the absorbance ratio for free coat protein preparations displaying various epitope fusions. In cases where the maximum to minimum ratio was lower than expected, e.g. Myc N, the coat protein preparation was treated with an anion exchange resin, such as DEAE Sepharose. The contaminating RNA associates strongly with the positively charged resin, while the coat protein's association will be lower, permitting selective elution of the coat protein at low chloride ion concentrations. This approach was successful at separating Myc N coat protein from contaminating residual RNA by a 50 mM NaCl elution, to yield a coat protein preparation with a maximum to minimum absorbance ratio greater then two (FIG. 15B to D)

TABLE 8

Ratio of absorbance maximum (282 nm) to absorbance minimum (251 nm) for free coat protein displaying various epitope fusions.

| Fusion | OD Ratio |
|---|---|
| HPV ep2 N | 2.1 |
| ELDKWAS (Seq ID No: 12) N | 2.2 |
| Myc C | 2 |
| Myc N | 1.22 |

Fusion location designation; N, N terminus; C, C terminus.

Figure 5:
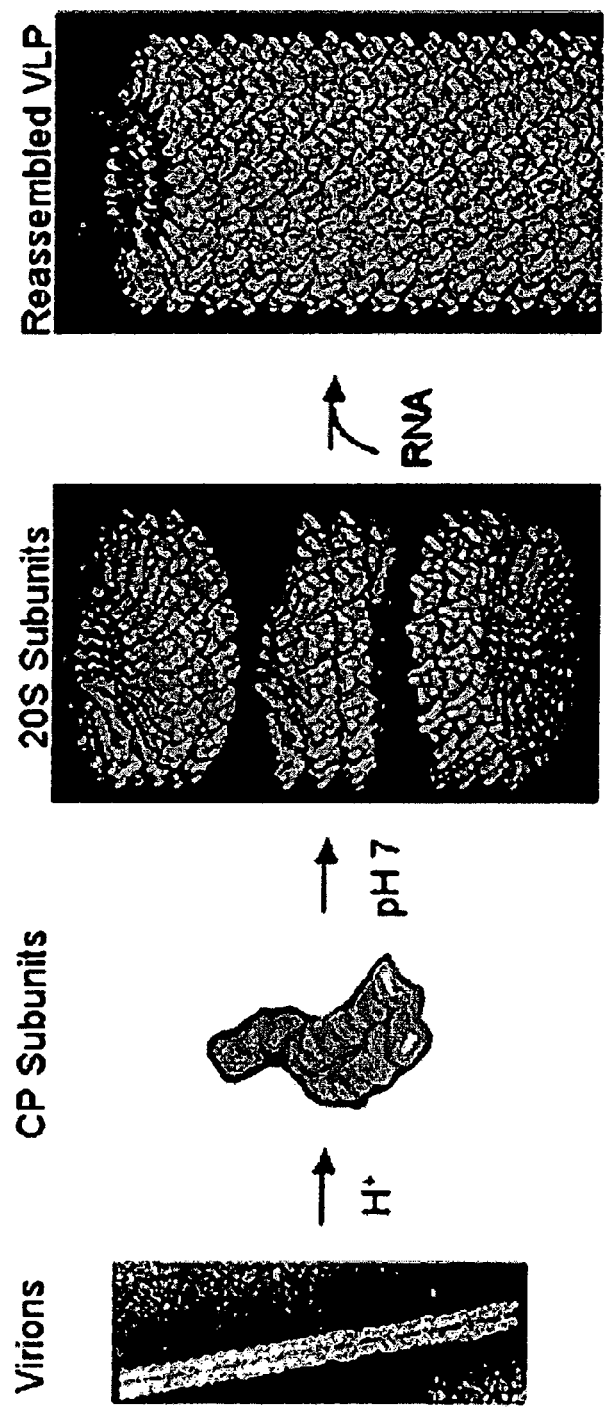

Prior to use in reassembly reactions, the coat protein preparation is converted from 4 S subunits, consisting of 3 to 4 coat proteins, to 20 S disks (see FIG. 5). This is accomplished by incubating the coat protein preparation at room temperature for 24 to 48 hours prior to use, under the correct pH and ionic strength conditions. For example, TMV U1 coat protein, in 0.1 M phosphate buffer, pH 7.0 was allowed to equilibrate to room temperature (20-22° C.), from 4° C., over 16 hours and the initial and equilibrated coat preparation was analyzed by size exclusion chromatography. As seen in FIG. 16, room temperature incubation results in a bimodal distribution, resulting from the formation of 20 S disks.

Example 10

Reassembly of Wild Type TMV Virions from 20S Disks

This Example, together with Examples 11-13, illustrate the methods for the generation of multivalent and bifunctional vaccines i.e. step S18 (FIG. 4) to yield P4 (FIG. 4). The standard conditions for TMV reassembly have been outlined for wild type U1 coat protein and a wild type TMV RNA scaffold (Fraenkel-Conrat, H and Singer, B (1959) Biochim Biophys Acta, 33, 359-370). Typically a 0.1 M phosphate or pyrophosphate buffer at a pH of 7.0 to 7.5 is employed with a mass ratio of coat protein to RNA of 22:1.

TMV U1 coat protein was generated from wild type virus isolated from *N. tabacum* var. MD609 plants, as described in Example 9. Wild type RNA was isolated from the same virus with the RNeasy Plant Mini Kit (Qiagen, Valencia, Calif.). Reassembly reactions were performed in 200 μl volumes, at a coat protein concentration of 1100 μg/ml and a RNA concentration of 50 μg/ml, in a 96 well plate format. The reactions were buffered with 0.1 M phosphate or pyrophosphate, pH 7.2 and the coat protein preincubated for two days at room temperature prior to use. This preincubation results in the formation of 20S disks from the 4 S subunits (FIG. 16). In addition to the standard conditions, the addition of the ribonuclease inhibitor RNasin to the 0.1 M phosphate buffered reaction was also tested. The reassembly reactions were followed by measuring the change in absorbance at 310 nm over time, which corresponds to the increase in the average length of the reassembly products.

FIG. 17A shows the A310 nm profiles for the reassembly reactions. The wild type virus control was such that the molar RNA concentration was equivalent to that of the reassembly reactions. The use of pyrophosphate in place of phosphate improved the initial rate of reassembly and the OD maximum corresponded to that of the TMV virus control. For the phosphate buffered reassembly reaction the maximum OD was lower than the virus trace (0.12 OD vs. 0.14 OD). Assessing the RNA integrity in the final reassembly reaction by agarose gel electrophoresis (FIG. 17B) indicated that RNA degradation was occurring in both the pyrophosphate and phosphate samples, and to a greater extent in the latter. The addition of different ribonuclease inhibitors to the coat protein was therefore tested. The ribonuclease inhibitor (either RNasin (Promega, Madison, Wis.) with and without additional DTT, or SUPERase (Ambion, Austin, Tex.)) was added to the coat protein preparation 30 minutes prior to RNA addition (0.2-4 U/ul). SUPERase at all concentrations tested was ineffective whereas the RNasin reduced RNA degradation substantially (FIG. 17B). The presence also improved the maximum OD 310 nm attained for the reassembly reaction (FIG. 17A).

To determine the functional significance of the different buffer combinations, aliquots of the reassembly reactions were analyzed by the local lesion host assay (Table 9). The reassembly reactions, naked RNA and virus controls were serially diluted and applied to the leaves of *N tobacum* 'Xanthi' NN plants, with carborundum employed as an abrasive. Five days post inoculation the lesion numbers were counted and provided a semi-quantitative measure of the titer of functional virus in the reassembly reactions.

TABLE 9

Local lesion host assay data for reassembly reactions with wild type U1 coat protein and TMV RNA.

| Dilution | Virus control | Free RNA control | Reassembly PO4 | Reassembly pyro PO4 | Reassembly PO4 RNasin |
|---|---|---|---|---|---|
| 10-2 | | 45 ± 13 | | | |
| 10-3 | | 4 ± 1 | | | |
| 10-4 | 123 ± 41 | 1 ± 1 | 25 ± 7 | 95 ± 31 | 122 ± 44 |
| 10-5 | 14 ± 10 | | | 6 ± 4 | 3 ± 1 | 19 ± 7 |

PO4, 0.1M phosphate buffered; pyro PO4, 0.1M pyrophosphate buffered; PO4 RNasin, 0.1M phosphate buffered with 0.4 U/μl RNasin ribonuclease inhibitor.

Comparing the infectivity of free RNA to the reassembly reactions, which contained an equivalent molar concentration of RNA, clearly illustrates the improvement in infectivity with RNA encapsidation. Within the reassembly reactions, a marked improvement in infectivity was evident for the phosphate buffer when RNasin was present, which correlated with the improvement in RNA integrity and A310 nm OD maximum. The observed infectivity with RNasin was comparable to that of the virus control. The pyrophosphate buffer also improved infectivity due to the accelerated reassembly, which aided in the protection of the RNA.

Example 11

Reassembly of Coat Protein Fusions onto TMV RNA

A central aim of this work is the generation of a multifunctional TMV-based reassembly product, which displays epitopes with different functionalities e.g. a cell targeting or immunomodulation sequence together with an antibody or CTL target. As a first step, the ability of various coat protein fusions to reassemble onto TMV RNA was examined. The fusions chosen were ELDKWAS (Seq ID No:12) and HPV ep2 at the N terminus and Myc at the C terminus. The reassembly reactions were performed in 200 μl volumes, at a coat protein concentration of 1100 μg/ml and a RNA concentration of 50 μg/ml, in a 96 well plate format. The reactions were buffered with 0.1 M phosphate, pH 7.0 and the coat protein preincubated for two days at room temperature prior to use. In a subset of the reactions the ribonuclease inhibitor RNasin was incorporated. The reassembly reactions were followed by measuring the change in absorbance at 310 nm over time, which corresponds to the increase in the average length of the reassembly products.

FIG. 18A shows the A310 nm profiles for the reassembly reactions involving the ELDKWAS (Seq ID No:12) coat protein fusion. The presence of RNasin in the reaction mixture clearly resulted in an improved absorbance profile with a higher final OD. The RNA integrity of the reassembly reactions was assessed by agarose gel electrophoresis (FIG. 18B). Although the extent of degradation was substantially higher than for the reassembly reactions involving U1 coat protein, the presence of RNasin did reduce the extent of RNA degradation in the ELDKWAS (Seq ID No:12) coat protein reassemblies.

The A310 nm kinetics together with the RNA profile suggest that RNasin increases the proportion of full-length rods formed during reassembly. To confirm this, samples were analyzed by electron microscopy (FIG. 19). Comparing the images for coat protein in the presence and absence of RNA shows that reassembly of the ELDKWAS (Seq ID No:12) coat protein fusion onto the TMV RNA scaffold occurred. To assess the influence of RNasin, the normalized particle size distribution, obtained from the electron microscopy images was determined. With RNasin present there was a reduction in the 0-100 nm length rods with a concurrent increase, from 5% to 20% of full length (>275 nm) rods, which correlates with the A310 nm absorbance data.

The reduction in full-length rods presumably results from the reduced pool of full length RNA. This would be expected to reduce the number of functional i.e. infectious reassembly products. Analysis of the reassembly products by the local lesion host assay confirmed this reduction; omission of RNasin reduced the average number of lesions observed by a factor of 9 (Table 10).

TABLE 10

Local lesion host assay data for reassembly reactions with multiple coat protein fusion and TMV RNA.

| Coat protein 1 | Coat protein 2 | Reassembly PO4 | Reassembly PO4 RNasin |
|---|---|---|---|
| ELDKWAS (Seq ID No: 12) (N) | — | 4 ± 6 | 37 ± 16 |
| Myc (C) | — | 2 ± 2 | 31 ± 17 |
| HPV ep2 (N) | — | 2 ± 1 | 11 ± 6 |
| ELDKWAS (Seq ID No: 12) (N) | HPV ep2 (N) | | 6 ± 4 |

TABLE 10-continued

Local lesion host assay data for reassembly reactions with multiple coat protein fusion and TMV RNA.

| Coat protein 1 | Coat protein 2 | Reassembly PO4 | Reassembly PO4 RNasin |
|---|---|---|---|
| ELDKWAS (Seq ID No: 12) (N) | Myc (C) | | 21 ± 13 |
| HPV ep2 (N) | Myc (C) | | 50 ± 43 |

PO4, 0.1M phosphate buffered; PO4 RNasin, 0.1M phosphate buffered with 0.4 U/μl RNasin ribonuclease inhibitor. All dilutions were at $10^{-3}$. At this dilution no lesions were detected for free wild type RNA. N, N terminal fusion; C, C terminal fusion.

Reassembly reactions were also performed with the HPV ep2 and the Myc coat protein fusions, in the presence or absence of RNasin. Similar to the ELDKWAS (Seq ID No:12) coat protein fusion, the presence of RNasin during the reassembly resulted in A310 nm profiles with a higher final OD and improved RNA integrity. From a functional standpoint the reassembly products generated in the presence of RNasin showed greater activity by the local lesion host assay (Table 10). For Myc and HPV ep2 the average number of lesions were 15 and 6 fold higher respectively when RNasin was present. These infectivity studies clearly illustrate the ability of a TMV coat protein carrying a solvent exposed epitope to reassemble and encapsidate a functional RNA.

The coat protein preparations do have a plant-derived ribonuclease activity associated with them, which can be partially mitigated by the inclusion of RNasin in the reassembly reaction. Alternative approaches can also be used to reduce the ribonuclease activity associated with the starting virion preparations, from which the coat protein preparations are generated. The virus preparation can be treated with bentonite, which inhibits ribonuclease activity (Jacoli, G., Ronald, W., and Lavkulich, L.: Inhibition of Ribonuclease Activity by Bentonite, Can J Biochem 51, 1558, 1973). Alternatively the virus preparation can be treated with diethylpyrocarbonate (DEPC) at 0.05%-0.1% v/v, which inactivates RNases by reacting specifically with the histidine residues in the enzymatic site. Residual DEPC is removed by dialyzing the treated virus extensively against any buffer containing a primary amine group, e.g. Tris(2-amino-2-hydroxymethyl-1,3-propanediol), with which DEPC reacts.

Figure 20:
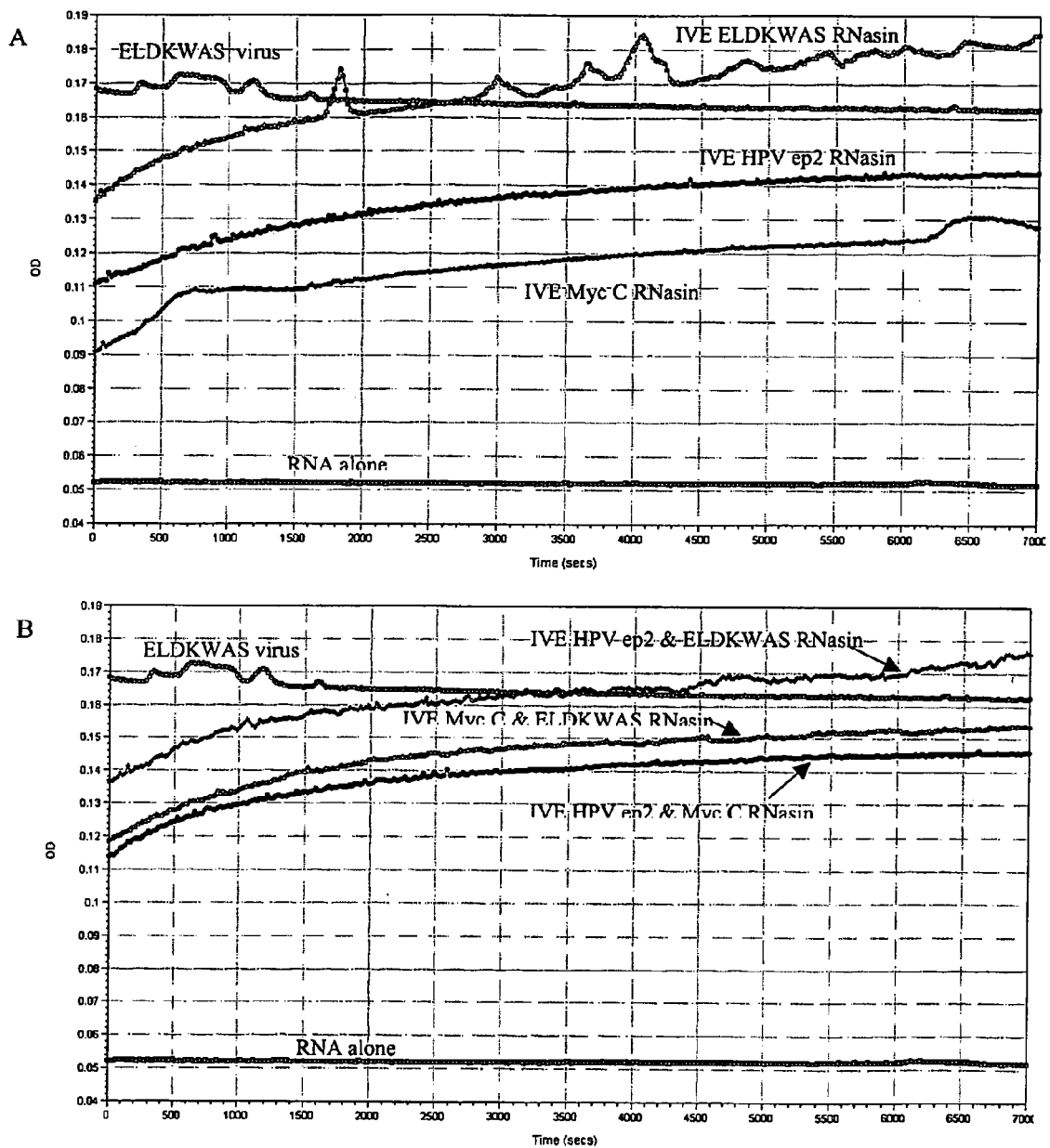

Reassembly reactions to generate a multivalent TMV-based vaccine were performed using a TMV RNA scaffold. The ELDKWAS (Seq ID No:12), Myc and HPV ep2 coat protein fusions were combined pair wise at a 1 to 1 ratio. FIG. 20 compares the A310 nm reassembly kinetics for the bivalent encapsidations to those for the coat protein fusions used individually. The bivalent reactions showed a similar rise in absorbance over time indicating that reassembly was occurring efficiently in the presence of two independent coat protein fusions. To test for the generation of functional bivalent reassembled virions, local lesion host assays were performed (Table 10). Lesion numbers comparable to the monovalent assemblies were obtained, confirming the presence of functional reassembly products.

Example 12

Multivalent Papillomavirus Prophylactic Vaccine Introduction

Animals may be protected against infection with papillomaviruses by vaccination with either or both papillomavirus structural proteins, L1 and L2 (Da Silva D M et al., 2001, Journal of Cellular Physiology 186:169-182; Koutsky L A et al., 2002, New England Journal of Medicine 347:1645-51). Protection against papillomavirus infection primarily requires a specific humoral response, which results in production of virus neutralizing antibodies (Nab) directed at epitopes in the structural proteins. A cellular immune response directed against the structural proteins may also contribute to vaccine-induced immunity. Live recombinant virus and DNA vaccine vectors carrying L1, or one or more of the non-structural genes E1, E2, E4, E6, E7 and E8, can induce protective immunity in vaccinated animals; in these cases both cellular and humoral immune responses are detected (Sundaram P et al., 1997, Vaccine 15:664-71; Moore R A et al. J Gen Virol 20:2299-301). It is well established that a humoral response directed against papillomavirus structural proteins is both necessary and sufficient for protective immunity against papillomavirus infection (Embers et al., 2002 Journal of Virology 76:9798-9805). A cellular immune response against virus-encoded proteins will enhance the level and robustness of the protective immune response, but will not prevent initial infection (Tobery T W et al., 2003, Vaccine 21: 1539-47).

Bivalent or Multivalent Reassembled Vaccines

The most important papillomavirus Nabs bind conformational epitopes in L1, and recognize only intact virus, or correctly assembled virus-like particles (VLP). These Nabs recognize epitopes in hypervariable loops on the capsid surface, and generally will only neutralize closely related papillomavirus types. Antibodies that bind linear epitopes in the N-terminal region of L2 may also neutralize virus infectivity. Most importantly, Nabs directed against L2 epitopes show the ability to cross-neutralize distinct viral strains (Embers M E et al., 2002; Journal of Virology 76:9798-9805; Kawana Y et al., 2001, Journal of Virology 75: 2331-2336; Kawana K et al., 1999, Journal of Virology 73:6188-6190; Kawana K et al. 2001, 1496-1502; Roden R B S et al., Virology 270:254-257). Embers et al. (2002; Journal of Virology 76:9798-9805) demonstrated that peptides that represent linear epitopes in the L2 proteins of the rabbit papillomaviruses rabbit oral papillomavirus (ROPV) and cottontail rabbit papillomavirus (CRPV) could induce good protective immunity against challenge with the homologous virus, but not against the heterologous virus.

Recombinant TMV U1 that display the linear, neutralizing rabbit papillomavirus epitopes CRPV L2.1; CRPV L2.2; ROPV L2.1 and ROPV L2.2 (Embers M E et al., 2002 Journal of Virology were constructed (Table 2). Each recombinant virus will induce neutralizing antibodies that will protect animals against challenge with high titer of homologous virus. However, each vaccine may not induce sufficient titer of Nabs to neutralize the heterologous virus.

Assembling at least two different coat proteins, each of which displays a different peptide, on a structural RNA that contains the TMV OAS, can make a multivalent recombinant vaccine that will induce protective immunity against both CRPV and ROPV. For example, the methods described in Example 9 may be used to isolate free coat protein from recombinant TMV virions that display the CRPV L2.1 peptide at the "GPAT" position proximal to the C terminus of TMV U1. Likewise, free coat protein may be isolated from recombinant TMV virions that display the ROPV L2.1 peptide at the "GPAT" position proximal to the C terminus of TMV U1. Wild type TMV RNA, or a recombinant RNA that contains that TMV U1 origin of assembly sequence (OAS) may be used as the scaffold on which the reassembled bivalent vaccine is built, according to methods described in Example 10 and 11. Similarly, additional recombinant U1 coat proteins that display peptides with the ability to induce Nabs in vaccinated animals may be incorporated into the reassembly reaction to generate a multivalent vaccine virus or virus-like particle. Animals that are vaccinated with bivalent or multivalent vaccines will produce antibodies that recognize the various peptide antigens fused to the recombinant vaccine molecule; these antibodies are capable of neutralizing both CRPV and ROPV. New Zealand white rabbits will thus be protected against infection against two distinct virus species after vaccination with a single vaccine moiety.

Multifunctional Vaccine: Induction of Humoral and Cellular Immunity

The sequences of human papillomavirus type 16 L2 that are homologous with the CRPV L2.1, ROPV L2.1; CRPV L2.2 and CRPV L2.2 peptides are capable of binding to specific receptors, and on binding to the cell surface are able to mediate cellular entry of proteins fused to these sequences by receptor-mediated mechanisms (Kawana Y et al., 2001 *Journal of Virology* 75: 2331-2336; Yang et al. 2003, *Journal of Virology* 77:3531-3541). It is thus expected that virions and reassembled virus-like structures that display these sequences will be able to bind to the surface of rabbit cells, and mediate entry of the reassembled virus structure into the cell. The additional cell fusion function of reassembled particles with one or more of the CRPV L2.1, ROPV L2.1; CRPV L2.2 and CRPV L2.2 peptides displayed by the assembled virus or virus-like particles allows delivery of a functional RNA payload to the cytoplasm of transduced cells.

To augment the protective antibody mediated immunity induced by the L2 peptides displayed on the surface of the reassembled viral structure, the RNA scaffold will have additional biological activity. For example, the scaffold RNA is a recombinant RNA molecule that encodes the Semliki forest alphavirus (SFV) RNA sequences that are required for autonomous replication, with the CRPV L1 gene that may be expressed under the control of the 26S RNA promoter from SFV, and the TMV U1 OAS inserted downstream of the CRPV L1 gene. This construct is shown in FIG. 22. Animals are immunized with reassembled virus structures that contain the capped SFV::CRPVL1::OAS RNA molecule as a scaffold, protected by recombinant TMV coat proteins that display one or more of the CRPV L2.1, ROPV L2.1; CRPV L2.2 and CRPV L2.2 epitopes assembled on the scaffold RNA. The recombinant TMV coat proteins perform several important functions: (1) they protect the recombinant SFV RNA molecule from nuclease digestion; (2) they form a particulate, quasicrystalline structure, such as are preferentially recognized and engulfed by macrophages, dendritic cells, and other antigen presenting cells; (3) through specific cell-binding activity, they deliver the recombinant particles to the cytoplasm.

Once the particles are in the cytoplasm, the recombinant RNA molecule is translated, and the RNA undergoes one or more cycles of replication mediated by the SFV non-structural proteins (NSP) replicase activity. The subgenomic RNA encoding the CRPV L1 RNA and TMV OAS is transcribed and the CRPV L1 RNA translated. The intracellularly expressed L1 protein is then available for processing and presentation via MHC Class I to T-cells, thereby priming a cellular immune response against the L1 protein. Replication of the recombinant SFV RNA delivered to the cytoplasm of transduced cells induces the innate immune response, via pathogen surveillance signaling molecules such as the dsRNA-induced protein kinase (PKR), resulting in secretion of inflammatory cytokines such as interferon gamma. This augments the specific cellular immune response induced against the L1 ORF. Thus, a broad, robust immune response against both structural proteins (L1 and L2) is induced. Rabbits vaccinated with these multifunctional vaccines are protected against challenge with both CRPV and ROPV viruses.

An alternative method to generate a functional RNA is to insert an IRES and coding sequence for L1 into TMV RNA, which also expresses a molecular fusion of L2 peptide epitope onto coat protein. This method has the advantage of encapsidating the RNA in vivo, and does not rely on reencapsidation to protect the RNA from degradation until after cellular uptake mechanisms allow for transcription of the gene. In a third strategy, the coat protein also carries an N terminal cysteine for conjugation of a T-helper epitope, a cell fusion epitope, an adjuvant, or the full-length gene product of a non-structural protein such as E7.

Papillomavirus nonstructural proteins, including E1, E2, E4, E6, E7 and E8 are known to mediate protective immunity, or lesion regression and clearance in vaccinated animals (Han R et al., 2002, *Cancer Detect Prev* 26:458-67; Han R et al., 2000. *Journal of Virology* 74: 9712-6). In the same manner as described above, mRNAs or autonomously replicating RNAs encoding other papillomavirus proteins which are known to mediate protective immunity, and which can induce regression or cure of virus infection, may be encapsidated within virus structures (FIG. 22).

Example 13

Multivalent Melanoma Vaccine

Melanoma antigens that stimulate good protection against tumor growth are typically characterized as CTL epitopes. CTL responses are highly dependant upon the context for antigen presentation, including immunostimulation during vaccine presentation to the immune system. This is characterized by a need for either immunostimulatory cytokines, such as GM-CSF or IFNγ, adjuvants that specifically activate T cells, such as CpG oligo, or immunomodulatory peptides or proteins, such as Il1B or MIP1a or IP10, to be delivered along with the vaccine, or fused directly to the vaccine product. Melanoma CTL epitope fusions, either molecular or chemical conjugates, are reassembled onto wild type TMV RNA and tested for appropriate stimulation of peptide specific CTL responses. The same melanoma CTL epitope fusions are then reassembled onto an RNA that contains both a TMV origin of assembly, and a mammalian translatable codon for IFNg, GM-CSF, MIP1a, or IP 10. After vaccination with epitope TMV or epitope TMV/IFNγ (for example), the level of CTL response is measured and compared. Translation of the functional RNA produces a protein that results in immune activation, thereby increasing the CTL response.

Alternatively, the RNA encodes a second full-length antigen that primes the cellular or humoral immune response for broader immune coverage. For example, melanoma tumors express several specific antigens that generate both CTL and antibody responses in challenged individuals. In murine tumors, such antigens include p15e, tryrosinase and GP100. Several CTL epitopes, as well as antibody stimulating domains, exist for each tumor specific antigen. Defined CTL epitopes, e.g. the p15e CTL epitope, are fused to the surface of TMV, and the encapsidated RNA encodes the entirety of gp100, or tyrosinase coding sequences. CTL reactivity to the p15e epitopes is measured, and further cellular or humoral reactivity to the gp100 or tyrosinase epitopes encoded by the RNA demonstrate RNA expression and activity of the resulting gene product.

Cellular or humoral assays indicate the level at which the vaccine is stimulating an immune response. Another way to show immune reactivity is by challenging animals with the tumor encoding those antigens and monitoring the rate of tumor growth, or the morbidity that that tumor causes. Such models exist for melanoma, and are widely used to prototype the effectiveness of melanoma vaccines. The B16 melanoma model expresses p15e, tryosinase, and gp100, and requires an effective CTL response after vaccination to reduce or eliminate the rate of tumor growth. Animals vaccinated with CTL epitope fusion vaccines are challenged with tumor, and an effective immune response will decrease the rate of tumor growth or morbidity compared to controls. If either an immunostimulatory RNA or full-length gene product encapsidated by a TMV coat or a TMV coat fusion is effective, then the rate of tumor growth should decrease compared to a protein vaccine alone, or the overall morbidity should decrease. These finding will corroborate the cellular and humoral response data, considering that these responses are essential to reducing or eliminating tumor.

As described above for papillomavirus applications, the functional encapsidated RNA can be self-replicating, such as an engineered alphavirus containing a TMV origin of assembly, or can contain an IRES, to stimulate translation from an internal site in TMV RNA (see FIG. 22 for examples). Also as described above, the combination of epitope fusions can be made either by molecular or chemical conjugation methods, and need not be limited to peptides. DNA sequences and whole proteins may also be added to reassembled TMV, or to TMV coat fusions that also encode an N-terminal cysteine.

Example 14

Immunogenicity of TMV Coat Protein Fusions

Immunogenicity to V5 and Myc U1 Coat Fusions: Responses to Antibody Epitopes

To verify that coat fusion peptides can stimulate appropriate immunity, we tested myc and V5 U1 peptide fusions, with known antibody binding properties, as vaccines in mice, and then looked for anti-myc and anti-V5 antibody responses. V5 and myc TMV U1 coat fusions were prepared by extraction methods, optimized for the recovery of the fusion of interest. Material was quantitated by the BCA protein assay, evaluated for peptide integrity by MALDI-TOF and for purity by SDS-PAGE. 10 μg of TMV protein was then injected into Balb-C mice three times, every two weeks. After the second and third vaccines, animals were bled and sera was collected and analyzed for peptide specific reactivity by ELISA. The results of serum titers after the third vaccination are show in FIG. 23, and are boosted from levels observed after two vaccines.

Results from this study indicate that at all three positions, V5 and myc peptide fusions to TMV U1 coat can elicit the appropriate anti-peptide antibody response even when given without adjuvant. Varied response levels in individual mice are typical of subunit vaccines, and have been observed for other antigen vaccines. Overall, the average response in each vaccine group tested was not significantly different by position of the peptide fusion, even though the maximum response levels differed significantly in each group. Interestingly, responses to the TMV carrier were generally lower in magnitude than the anti-peptide response (data not shown). Of note, these vaccines were administered without adjuvant, and the high levels of responses in each group show that the viral carrier can provide humoral immune stimulation that is antigen specific.

CTL Response Assay Development for Ova Peptide U1 Coat Fusions

In addition to testing the ability of antibody-target peptides to stimulate appropriate humoral responses in vaccinated mice, we also tested the ability of a CTL epitope, derived from the chicken ovalbumin protein, to stimulate appropriate cellular immunity in appropriately MHC restricted mice. 20 μg Ova-N or Ova-G TMV fusions were administered 4 times every two weeks without adjuvant to mice, and then spleens were harvested from vaccinated animals five days after the final vaccine. Cells were isolated, cultured with either media or media plus ova peptide for 5 hours in the presence of the Golgi transport inhibitor Brefeldin A, and then cells were fluorescently stained with FITC conjugated antibodies against surface expression of CD4 and CD8 T cell receptors, in conjunction with PE staining of the intracellular cytokines IFN gamma or TNF alpha. Stimulation with ova peptide should upregulate these cytokines in T cells that are specific for the peptide, and be measured by an increase in cell number by Fluorescence Activated Cell Sorting (FACS). $5 \times 10^5$ events were collected, about 20% of which are T cells.

Both CD4 and CD8 cells were monitored for increased intracellular expression of IFN γ (gamma) and TNF α (alpha). As shown in FIG. 24, after a five-hour peptide stimulation, intracellular IFN gamma levels rose in CD4 positive cells (from 0.08% of gated events to 0.17% or 10 to 22 cells), and in CD8 positive cells (from 0.08% of gated events to 0.13% or 11 to 17 cells; data not shown), which represent statistically significant increases. TNF alpha levels rose significantly in CD4+ cells (0.08 to 0.13%) but did not change in CD8+ cells (0.12% to 0.10%; data not shown).

Considering that no adjuvant was administered with the vaccine, these modest increases in cytokine levels suggest that the vaccine is stimulating an appropriate cellular response. Administration of an adjuvant with the vaccine, or the fusion of immunostimulatory peptides to the TMV vaccine, is expected to increase the percentage of activated T cells. For example, the T cell activating adjuvant, single stranded CpG DNA oligo 1758, specifically augments cellular responses in ova and other CTL systems. For our system the nucleotides are either mixed with the vaccine, or fused directly to TMV U1. In other systems, the IL1b peptide has been shown to augment both antibody and CTL responses but only if the IL1b peptide is physically linked to the ova peptide vaccine, such as in a multivalent vaccine.

What is claimed is:

1. A method for making a virus-like particle (VLP) containing multiple, different composition peptides or proteins displayed by a process comprising the steps of: a) disassembling separate VLP populations, each displaying a distinct peptide or protein via genetic fusion; b) disassembling a separate VLP population that has a surface residue for chemical conjugation, provided by genetic fusion; c) forming encapsidation intermediate populations such that: i) each displays a distinct peptide or protein and ii) each displays a surface residue for chemical conjugation; d) effecting chemical conjugation of unique peptide, protein or nucleic acid moieties to separate populations of the encapsidation intermediate displaying surface residue for chemical conjugation; e) mixing encapsidation intermediates from different populations displaying peptides or proteins by genetic fusion or displaying peptides, proteins or nucleic acids by chemical conjugation; f) forming intact VLP surrounding a nucleic acid core that is composed of different encapsidation intermediates such that the VLP displays more than one moiety, be it peptide, protein or nucleic acid, or some combination of these moieties.

2. A method as set forth in claim 1, wherein the VLPs are TMV virus and the encapsidation intermediates are 20S disks.

3. A method as set forth in claim 1, wherein the chemical conjugation of unique peptide and/or nucleic acid moieties to the encapsidation intermediates, displaying the residues for chemical conjugations, is performed following the formation of an intact VLP surrounding a nucleic acid core.

* * * * *